(12) United States Patent
Saadat et al.

(10) Patent No.: US 11,602,260 B2
(45) Date of Patent: Mar. 14, 2023

(54) METHOD AND DEVICE FOR IMAGE GUIDED POST-NASAL NERVE ABLATION

(71) Applicant: Arrinex, Inc., Redwood City, CA (US)

(72) Inventors: Vahid Saadat, Atherton, CA (US); Mojgan Saadat, Atherton, CA (US); William Jason Fox, San Mateo, CA (US)

(73) Assignee: Arrinex, Inc., Redwood City, CA (US)

( * ) Notice: Subject to any disclaimer, the term of this patent is extended or adjusted under 35 U.S.C. 154(b) by 801 days.

(21) Appl. No.: 15/431,740

(22) Filed: Feb. 13, 2017

(65) Prior Publication Data
US 2017/0231474 A1    Aug. 17, 2017

Related U.S. Application Data

(60) Provisional application No. 62/294,142, filed on Feb. 11, 2016.

(51) Int. Cl.
*A61B 1/00* (2006.01)
*A61B 1/005* (2006.01)
(Continued)

(52) U.S. Cl.
CPC ........ *A61B 1/00087* (2013.01); *A61B 1/0014* (2013.01); *A61B 1/0051* (2013.01);
(Continued)

(58) Field of Classification Search
CPC ............ A61B 1/00082; A61B 1/00087; A61B 1/00094; A61B 1/00098; A61B 1/00135;
(Continued)

(56) References Cited

U.S. PATENT DOCUMENTS 5,527,351 A    6/1996    Friedman et al.
5,611,796 A    3/1997    Kamami
(Continued)

FOREIGN PATENT DOCUMENTS

EP    2532300    12/2012
EP    2662027    11/2013
(Continued)

OTHER PUBLICATIONS

Bicknell et al., "Cryosurrgery for Allergic and Vasomotor Rhinitis", The Journal of Laryngology and Otology, vol. 93, Feb. 1979, 143-146.
(Continued)

*Primary Examiner* — Alexandra L Newton
*Assistant Examiner* — Alexandra Newton Surgan
(74) *Attorney, Agent, or Firm* — McDonnell Boehnen Hulbert & Berghoff LLP

(57) ABSTRACT

Devices and methods for treating rhinitis are provided. An integrated therapy and imaging device is provided for single handheld use. The device may have a hollow elongated cannula, a therapeutic element coupled to a distal portion of the cannula, an imaging assembly coupled to the cannula to provide visualization of the therapeutic element, and an articulating region operably coupled to the imaging assembly to articulate the imaging assembly. The imaging assembly may be articulated so as to translate vertically, laterally, axially, and/or rotationally.

45 Claims, 28 Drawing Sheets

(51) Int. Cl.
*A61B 1/06* (2006.01)
*A61B 1/015* (2006.01)
*A61B 1/05* (2006.01)
*A61B 1/233* (2006.01)
*A61B 18/02* (2006.01)
*A61B 18/22* (2006.01)
*A61B 90/00* (2016.01)
*A61B 18/06* (2006.01)
*A61B 18/14* (2006.01)
*A61B 18/24* (2006.01)
*A61B 90/30* (2016.01)
*A61B 34/20* (2016.01)
*A61B 18/00* (2006.01)
*A61B 18/18* (2006.01)

(52) U.S. Cl.
CPC ...... *A61B 1/00052* (2013.01); *A61B 1/00066* (2013.01); *A61B 1/00082* (2013.01); *A61B 1/00091* (2013.01); *A61B 1/00094* (2013.01); *A61B 1/00096* (2013.01); *A61B 1/00098* (2013.01); *A61B 1/00105* (2013.01); *A61B 1/00181* (2013.01); *A61B 1/015* (2013.01); *A61B 1/05* (2013.01); *A61B 1/0625* (2022.02); *A61B 1/0676* (2013.01); *A61B 1/233* (2013.01); *A61B 18/02* (2013.01); *A61B 18/06* (2013.01); *A61B 18/1492* (2013.01); *A61B 18/22* (2013.01); *A61B 18/24* (2013.01); *A61B 90/361* (2016.02); *A61B 2018/0022* (2013.01); *A61B 2018/00327* (2013.01); *A61B 2018/00434* (2013.01); *A61B 2018/00577* (2013.01); *A61B 2018/00714* (2013.01); *A61B 2018/00982* (2013.01); *A61B 2018/00994* (2013.01); *A61B 2018/0212* (2013.01); *A61B 2018/1861* (2013.01); *A61B 2034/2057* (2016.02); *A61B 2090/309* (2016.02); *A61B 2090/3614* (2016.02); *A61B 2218/002* (2013.01); *A61B 2218/007* (2013.01)

(58) Field of Classification Search
CPC ....... A61B 1/0014; A61B 1/0051; A61B 1/01; A61B 1/012; A61B 1/0125; A61B 1/018; A61B 1/233; A61B 1/00052; A61B 1/00114; A61B 1/00121; A61B 2018/00982; A61B 90/361; A61M 2210/0681

See application file for complete search history.

(56) References Cited

U.S. PATENT DOCUMENTS

| | | | |
|---|---|---|---|
| 5,733,280 A | 3/1998 | Avitall | |
| 5,843,077 A | 12/1998 | Edwards | |
| 5,899,898 A | 5/1999 | Arless et al. | |
| 5,899,899 A | 5/1999 | Arless et al. | |
| 5,971,979 A | 10/1999 | Joye et al. | |
| 6,045,549 A | 4/2000 | Smethers et al. | |
| 6,106,518 A | 8/2000 | Wittenberger et al. | |
| 6,210,355 B1 | 4/2001 | Edwards et al. | |
| 6,270,476 B1 | 8/2001 | Santoianni et al. | |
| 6,277,064 B1 | 8/2001 | Yoon et al. | |
| 6,283,959 B1 | 9/2001 | Lalonde et al. | |
| 6,355,029 B1 | 3/2002 | Joye et al. | |
| 6,361,531 B1 * | 3/2002 | Hissong | A61N 7/02 600/437 |
| 6,375,654 B1 | 4/2002 | McIntyre | |
| 6,428,534 B1 | 8/2002 | Joye et al. | |
| 6,432,102 B2 | 8/2002 | Joye et al. | |
| 6,514,245 B1 | 2/2003 | Williams et al. | |
| 6,517,533 B1 | 2/2003 | Swaminathan | |
| 6,537,271 B1 | 3/2003 | Murray et al. | |
| 6,575,966 B2 | 6/2003 | Lane et al. | |
| 6,595,988 B2 | 7/2003 | Wittenberger et al. | |
| 6,602,276 B2 | 8/2003 | Dobak, III et al. | |
| 6,648,879 B2 | 11/2003 | Joye et al. | |
| 6,666,858 B2 | 12/2003 | Lafontaine | |
| 6,673,066 B2 | 1/2004 | Werneth | |
| 6,685,732 B2 | 2/2004 | Kramer | |
| 6,736,809 B2 | 5/2004 | Capuano et al. | |
| 6,786,900 B2 | 9/2004 | Joye et al. | |
| 6,786,901 B2 | 9/2004 | Joye et al. | |
| 6,811,550 B2 | 11/2004 | Holland et al. | |
| 6,875,209 B2 | 4/2005 | Zvuloni et al. | |
| 6,905,494 B2 | 6/2005 | Yon et al. | |
| 6,908,462 B2 | 6/2005 | Joye et al. | |
| 6,949,096 B2 | 9/2005 | Davison et al. | |
| 6,972,015 B2 | 12/2005 | Joye et al. | |
| 6,989,009 B2 | 1/2006 | Lafontaine | |
| 6,991,631 B2 | 1/2006 | Woloszko et al. | |
| 7,001,378 B2 | 2/2006 | Yon et al. | |
| 7,060,062 B2 | 6/2006 | Joye et al. | |
| 7,081,112 B2 | 7/2006 | Joye et al. | |
| 7,101,368 B2 | 9/2006 | Lafontaine | |
| 7,104,984 B2 | 9/2006 | Ryba et al. | |
| 7,189,227 B2 | 3/2007 | Lafontaine | |
| 7,288,089 B2 | 10/2007 | Yon et al. | |
| 7,291,144 B2 | 11/2007 | Dobak, III et al. | |
| 7,300,433 B2 | 11/2007 | Lane et al. | |
| 7,354,434 B2 | 4/2008 | Zvuloni et al. | |
| 7,418,292 B2 | 8/2008 | Shafer et al. | |
| 7,442,190 B2 | 10/2008 | Abbound et al. | |
| 7,449,018 B2 | 11/2008 | Kramer | |
| 7,527,622 B2 | 5/2009 | Lane et al. | |
| 7,641,679 B2 | 1/2010 | Joye et al. | |
| 7,648,497 B2 | 1/2010 | Lane et al. | |
| 7,727,191 B2 | 6/2010 | Mihalik et al. | |
| 7,727,228 B2 | 6/2010 | Abboud et al. | |
| 7,740,627 B2 | 6/2010 | Gammie et al. | |
| 7,769,442 B2 | 8/2010 | Shafer et al. | |
| 7,794,455 B2 | 9/2010 | Abboud et al. | |
| 7,842,031 B2 | 11/2010 | Abboud et al. | |
| 7,862,557 B2 | 1/2011 | Joye et al. | |
| 7,892,230 B2 | 2/2011 | Woloszko | |
| 8,043,283 B2 | 10/2011 | Dobak, III et al. | |
| 8,043,351 B2 | 10/2011 | Yon et al. | |
| 8,088,127 B2 | 1/2012 | Mayse et al. | |
| 8,142,424 B2 | 3/2012 | Swanson et al. | |
| 8,157,794 B2 | 4/2012 | Dobak, III et al. | |
| 8,177,779 B2 | 5/2012 | Joye et al. | |
| 8,187,261 B2 | 5/2012 | Watson | |
| 8,231,613 B2 | 7/2012 | Baxter et al. | |
| 8,235,976 B2 | 8/2012 | Lafontaine | |
| 8,292,887 B2 | 10/2012 | Woloszko et al. | |
| 8,298,217 B2 | 10/2012 | Lane et al. | |
| 8,333,758 B2 | 12/2012 | Joye et al. | |
| 8,382,746 B2 | 2/2013 | Williams et al. | |
| 8,382,747 B2 | 2/2013 | Abboud et al. | |
| 8,388,600 B1 | 3/2013 | Eldredge et al. | |
| 8,394,075 B2 | 3/2013 | Ansarinia et al. | |
| 8,425,456 B2 | 4/2013 | Mihalik et al. | |
| 8,425,457 B2 | 4/2013 | Chang et al. | |
| 8,439,906 B2 | 5/2013 | Watson | |
| 8,465,481 B2 | 6/2013 | Mazzone et al. | |
| 8,475,440 B2 | 7/2013 | Abboud et al. | |
| 8,480,664 B2 | 7/2013 | Watson et al. | |
| 8,491,636 B2 | 7/2013 | Abboud et al. | |
| 8,512,229 B2 | 8/2013 | Saadat et al. | |
| 8,512,324 B2 | 8/2013 | Abboud et al. | |
| 8,545,491 B2 | 10/2013 | Abboud et al. | |
| 8,591,504 B2 | 11/2013 | Tin | |
| 8,617,149 B2 | 12/2013 | Lafontaine et al. | |
| 8,632,529 B2 | 1/2014 | Bencini | |
| 8,663,211 B2 | 3/2014 | Fourkas et al. | |
| 8,672,930 B2 | 3/2014 | Wittenberger | |
| 8,676,324 B2 | 3/2014 | Simon et al. | |
| 8,679,104 B2 | 3/2014 | Abboud et al. | |
| 8,679,105 B2 | 3/2014 | Wittenberger et al. | |
| 8,715,274 B2 | 5/2014 | Watson | |
| 8,715,275 B2 | 5/2014 | Burger et al. | |

(56) References Cited

U.S. PATENT DOCUMENTS

| | | |
|---|---|---|
| 8,747,401 B2 | 6/2014 | Gonzalez et al. |
| 8,764,740 B2 | 7/2014 | Watson |
| 8,771,264 B2 | 7/2014 | Abboud et al. |
| 8,827,952 B2 | 9/2014 | Subramaniam et al. |
| 8,900,222 B2 | 12/2014 | Abboud et al. |
| 8,911,434 B2 | 12/2014 | Wittenberger |
| 8,926,602 B2 | 1/2015 | Pageard |
| 8,936,594 B2 | 1/2015 | Wolf et al. |
| 8,945,107 B2 | 2/2015 | Buckley et al. |
| 8,986,293 B2 | 3/2015 | Desrochers |
| 8,986,301 B2 | 3/2015 | Wolf et al. |
| 8,996,137 B2 | 3/2015 | Wardle et al. |
| 9,050,073 B2 | 6/2015 | Newell et al. |
| 9,050,074 B2 | 6/2015 | Joye et al. |
| 9,060,754 B2 | 6/2015 | Buckley et al. |
| 9,060,755 B2 | 6/2015 | Buckley et al. |
| 9,066,713 B2 | 6/2015 | Turovskiy |
| 9,072,597 B2 | 7/2015 | Wolf et al. |
| 9,084,590 B2 | 7/2015 | Wittenberger et al. |
| 9,084,592 B2 | 7/2015 | Wu et al. |
| 9,089,314 B2 | 7/2015 | Wittenberger |
| 9,168,079 B2 | 10/2015 | Lalonde |
| 9,168,081 B2 | 10/2015 | Williams et al. |
| 9,179,964 B2 | 11/2015 | Wolf et al. |
| 9,179,967 B2 | 11/2015 | Wolf et al. |
| 9,211,393 B2 | 12/2015 | Hu et al. |
| 9,220,556 B2 | 12/2015 | Lalonde et al. |
| 9,237,924 B2 | 1/2016 | Wolf et al. |
| 9,241,752 B2 | 1/2016 | Nash et al. |
| 9,254,166 B2 | 2/2016 | Aluru et al. |
| 9,265,956 B2 | 2/2016 | Ackermann et al. |
| 9,333,023 B2 | 5/2016 | Wittenberger |
| 9,414,878 B1 | 8/2016 | Wu et al. |
| 9,415,194 B2 | 8/2016 | Wolf et al. |
| 9,433,463 B2 | 9/2016 | Wolf et al. |
| 9,439,709 B2 | 9/2016 | Duong et al. |
| 9,445,859 B2 | 9/2016 | Pageard |
| 9,452,010 B2 | 9/2016 | Wolf et al. |
| 9,480,521 B2 | 11/2016 | Kim et al. |
| 9,486,278 B2 | 11/2016 | Wolf et al. |
| 9,522,030 B2 | 12/2016 | Harmouche et al. |
| 9,526,571 B2 | 12/2016 | Wolf et al. |
| 9,555,223 B2 | 1/2017 | Abboud et al. |
| 9,572,536 B2 | 2/2017 | Abboud et al. |
| 9,801,752 B2 | 10/2017 | Wolf et al. |
| 2002/0049367 A1 | 4/2002 | Irion et al. |
| 2003/0144659 A1 | 7/2003 | Edwards et al. |
| 2004/0024412 A1 | 2/2004 | Clements et al. |
| 2006/0063973 A1 | 3/2006 | Makower et al. |
| 2006/0235474 A1 | 10/2006 | Demarais et al. |
| 2006/0276852 A1 | 12/2006 | Demarais et al. |
| 2007/0093710 A1 | 4/2007 | Maschke et al. |
| 2007/0173899 A1 | 7/2007 | Levin et al. |
| 2007/0179380 A1* | 8/2007 | Grossman ............ A61B 5/0073 600/462 |
| 2007/0265687 A1 | 11/2007 | Deem et al. |
| 2007/0293726 A1 | 12/2007 | Goldfarb et al. |
| 2007/0299433 A1 | 12/2007 | Williams et al. |
| 2008/0009851 A1 | 1/2008 | Wittenberger et al. |
| 2008/0009925 A1 | 1/2008 | Abboud et al. |
| 2008/0027423 A1* | 1/2008 | Choi ................ A61B 17/2202 606/40 |
| 2008/0082045 A1 | 4/2008 | Goldfarb et al. |
| 2008/0119693 A1* | 5/2008 | Makower ........... A61B 1/00135 600/114 |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0171271 A1 | 7/2009 | Webster et al. |
| 2009/0182193 A1 | 7/2009 | Whitman et al. |
| 2009/0182318 A1 | 7/2009 | Abboud et al. |
| 2009/0234345 A1 | 9/2009 | Hon et al. |
| 2009/0326318 A1* | 12/2009 | Tognaccini ............ A61B 34/30 600/104 |
| 2010/0057150 A1 | 3/2010 | Demarais et al. |
| 2010/0121270 A1 | 5/2010 | Gunday et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2011/0152855 A1 | 6/2011 | Mayse et al. |
| 2011/0184402 A1 | 7/2011 | Baust et al. |
| 2012/0029493 A1 | 2/2012 | Wittenberger et al. |
| 2012/0088968 A1* | 4/2012 | Gambhir ............ A61B 1/00075 600/106 |
| 2013/0006326 A1 | 1/2013 | Ackermann et al. |
| 2013/0018366 A1 | 1/2013 | Wu et al. |
| 2013/0218151 A1 | 8/2013 | Mihalik et al. |
| 2013/0253387 A1 | 9/2013 | Bonutti et al. |
| 2013/0281778 A1 | 10/2013 | Suehara et al. |
| 2013/0310822 A1 | 11/2013 | Mayse et al. |
| 2013/0345700 A1 | 12/2013 | Hlavka et al. |
| 2014/0058369 A1 | 2/2014 | Hon |
| 2014/0186341 A1 | 7/2014 | Mayse et al. |
| 2014/0207130 A1 | 7/2014 | Fourkas et al. |
| 2014/0228875 A1 | 8/2014 | Saadat et al. |
| 2014/0236148 A1 | 8/2014 | Hlavka et al. |
| 2014/0257271 A1 | 9/2014 | Mayse et al. |
| 2014/0276792 A1 | 9/2014 | Kaveckis et al. |
| 2014/0277429 A1 | 9/2014 | Kuzma et al. |
| 2014/0316310 A1 | 10/2014 | Ackermann et al. |
| 2014/0371812 A1 | 12/2014 | Ackermann et al. |
| 2015/0031946 A1 | 1/2015 | Saadat et al. |
| 2015/0045781 A1 | 2/2015 | Abboud et al. |
| 2015/0080870 A1 | 3/2015 | Wittenberger |
| 2015/0119868 A1 | 4/2015 | Lalonde et al. |
| 2015/0126986 A1 | 5/2015 | Kelly et al. |
| 2015/0157382 A1 | 6/2015 | Avitall et al. |
| 2015/0164571 A1* | 6/2015 | Saadat ............... A61B 18/1485 600/109 |
| 2015/0190042 A1* | 7/2015 | Segawa ............ G02B 23/2476 600/104 |
| 2015/0190188 A1 | 7/2015 | Lalonde |
| 2015/0196345 A1 | 7/2015 | Newell et al. |
| 2015/0196740 A1 | 7/2015 | Mallin et al. |
| 2015/0223860 A1 | 8/2015 | Wittenberger et al. |
| 2015/0238754 A1 | 8/2015 | Loudin et al. |
| 2015/0250524 A1 | 9/2015 | Moriarty et al. |
| 2015/0265329 A1 | 9/2015 | Lalonde et al. |
| 2015/0265812 A1 | 9/2015 | Lalonde |
| 2015/0313661 A1 | 11/2015 | Wu et al. |
| 2016/0022992 A1 | 1/2016 | Franke et al. |
| 2016/0038212 A1* | 2/2016 | Ryba ..................... A61B 18/02 606/21 |
| 2016/0045277 A1 | 2/2016 | Lin et al. |
| 2016/0066975 A1 | 3/2016 | Fourkas et al. |
| 2016/0074090 A1 | 3/2016 | Lalonde et al. |
| 2016/0114163 A1 | 4/2016 | Loudin et al. |
| 2016/0114172 A1 | 4/2016 | Loudin et al. |
| 2016/0012118 A1 | 5/2016 | Franke et al. |
| 2016/0128549 A1* | 5/2016 | Juergens ............ A61B 1/00112 600/112 |
| 2016/0143683 A1 | 5/2016 | Aluru et al. |
| 2016/0158548 A1 | 6/2016 | Ackermann et al. |
| 2016/0166305 A1 | 6/2016 | Nash et al. |
| 2016/0166306 A1 | 6/2016 | Pageard |
| 2016/0220295 A1 | 8/2016 | Wittenberger |
| 2016/0287315 A1 | 10/2016 | Wolf et al. |
| 2016/0317794 A1 | 11/2016 | Saadat |
| 2016/0331433 A1 | 11/2016 | Wu et al. |
| 2016/0331459 A1 | 11/2016 | Townley et al. |
| 2016/0354134 A1 | 12/2016 | Pageard |
| 2016/0354135 A1 | 12/2016 | Saadat |
| 2016/0354136 A1 | 12/2016 | Saadat |
| 2016/0361112 A1 | 12/2016 | Wolf et al. |
| 2017/0007316 A1 | 1/2017 | Wolf et al. |
| 2017/0014258 A1 | 1/2017 | Wolf et al. |
| 2017/0042601 A1 | 2/2017 | Kim et al. |
| 2017/0056087 A1 | 3/2017 | Buckley et al. |
| 2017/0056632 A1 | 3/2017 | Jenkins et al. |

(56) References Cited

U.S. PATENT DOCUMENTS

FOREIGN PATENT DOCUMENTS

| | | |
|---|---|---|
| EP | 2662046 | 11/2013 |
| EP | 2662116 | 11/2013 |
| WO | 99020185 | 4/1999 |
| WO | 9927862 | 6/1999 |
| WO | 99030655 | 6/1999 |
| WO | 0009053 | 2/2000 |
| WO | 0047118 | 8/2000 |
| WO | 0054684 | 9/2000 |
| WO | 0164145 | 9/2001 |
| WO | 01095819 | 12/2001 |
| WO | 0204042 | 1/2002 |
| WO | 0207628 | 4/2002 |
| WO | 02069862 | 9/2002 |
| WO | 0200128 | 11/2002 |
| WO | 02083196 | 2/2003 |
| WO | 03013653 | 2/2003 |
| WO | 03026719 | 4/2003 |
| WO | 03051214 | 6/2003 |
| WO | 03028524 | 10/2003 |
| WO | 03020334 | 12/2003 |
| WO | 03088857 | 12/2003 |
| WO | 2004000092 | 12/2003 |
| WO | 2005089853 | 11/2005 |
| WO | 2004108207 | 12/2005 |
| WO | 2006002337 | 1/2006 |
| WO | 2006118725 | 11/2006 |
| WO | 2006119615 | 11/2006 |
| WO | 2006124176 | 11/2006 |
| WO | 2006017073 | 4/2007 |
| WO | 2007145759 | 12/2007 |
| WO | 2008000065 | 1/2008 |
| WO | 2008042890 | 4/2008 |
| WO | 2008046183 | 4/2008 |
| WO | 2008051918 | 5/2008 |
| WO | 2008157042 | 12/2008 |
| WO | 2009114701 | 9/2009 |
| WO | 2009146372 | 12/2009 |
| WO | 2010081221 | 7/2010 |
| WO | 2010083281 | 7/2010 |
| WO | 2010111122 | 9/2010 |
| WO | 2011014812 | 2/2011 |
| WO | 2011091507 | 8/2011 |
| WO | 2011091508 | 8/2011 |
| WO | 2011091509 | 8/2011 |
| WO | 2011091533 | 8/2011 |
| WO | 2012012868 | 2/2012 |
| WO | 2012012869 | 2/2012 |
| WO | 2012015636 | 2/2012 |
| WO | 2012019156 | 2/2012 |
| WO | 2012051697 | 4/2012 |
| WO | 2012027641 | 5/2012 |
| WO | 2012058156 | 5/2012 |
| WO | 2012058159 | 5/2012 |
| WO | 2012058160 | 5/2012 |
| WO | 2012058161 | 5/2012 |
| WO | 2012058165 | 5/2012 |
| WO | 2012058167 | 5/2012 |
| WO | 2012174161 | 12/2012 |
| WO | 2013035192 | 3/2013 |
| WO | 2013110156 | 8/2013 |
| WO | 2013173481 | 11/2013 |
| WO | 2013163325 | 2/2014 |
| WO | 2014113864 | 7/2014 |
| WO | 2014138866 | 9/2014 |
| WO | 2014138867 | 9/2014 |
| WO | 2015038523 | 3/2015 |
| WO | 2015048806 | 4/2015 |
| WO | 2015061883 | 5/2015 |
| WO | 2015081420 | 6/2015 |
| WO | 2015106335 | 7/2015 |
| WO | 2015114038 | 8/2015 |
| WO | 2015139117 | 9/2015 |
| WO | 2015139118 | 9/2015 |
| WO | 2015153696 | 10/2015 |
| WO | 2016183337 | 11/2016 |
| WO | 2016186964 | 11/2016 |
| WO | 2017034705 | 3/2017 |
| WO | 2017047543 | 3/2017 |
| WO | 2017047545 | 3/2017 |
| WO | 2017139805 | 8/2017 |

OTHER PUBLICATIONS

Bluestone et al., "Intranasal Freezing for Severe Epistaxis", Arch Otolaryng, vol. 85, Apr. 1967, 119-121.

Costa et al., "Radiographic and Anatomic Characterization of the Nasal Septal Swell Body", Arch Otolaryngol Head Neck Surg., vol. 136, No. 11, Nov. 2010, 1109.

Sanu , "Two Hundred Years of Controversy Between UK and USA", Rhinology, 86-91.

Settipane et al., "Update on Nonallergic Rhinitis", Annals of Allergy Asthma & Immunology, vol. 86, 2001, 494-508.

Arora et al., "Cryodestruction of Vidian Nerve Branches", Indian Journal of Otolaryngology, vol. 32, No. 3, Sep. 1980, pp. 80-82.

Bumsted , "Cryotherapy for Chronic Vasomotor Rhinitis: Technique and Patient Selection for Improved Results", Laryngoscope, vol. 94, Apr. 1984, pp. 539-544.

Girdhar-Gopal , "An Assessment of Postganglionic Cryoneurolysis for Managing Vasomotor Rhinitis", American Journal of Rhinology, vol. 8, No. 4,, Jul.-Aug. 1994, pp. 157-164.

Golhar et al., "The effect of Cryodestruction of Vidian Nasal Branches on Nasal Mucus Flow in Vasomotor Rhinitis", Indian Journal of Otolaryngology, vol. 33, No. 1, Mar. 1981, pp. 12-14.

Goode , "A Liquid Nitrogen Turbinate Probe for Hypertrophic Rhinitis", Arch Otolaryngol., vol. 103, 1977, p. 431.

Mehra et al., "Cryosurgery in Vasomotor Rhinitis—An Analysis of 156 Patients", Indian Journal of Otolaryngology, vol. 42, No. 3, Sep. 1990, pp. 95-98.

Ozenberger , "Cryosurgery for the Treatment of Chronic Rhinitis", Laryngoscope, vol. 83, No. 4, 1973, pp. 508-516.

Ozenberger , "Cryosurgery in Chronic Rhinitis", The Laryngoscope, vol. 80, No. 5, May 1970, pp. 723-734.

Principato , "Chronic Vasomotor Rhinitis: Cryogenic and Other Surgical Modes of Treatment", The Laryngoscope, vol. 89, 1979, pp. 619-638.

Rao , "Cryosurgery on Inferior turbinate hypertrophy under topical anaesthesia—is it boon in electricity deprived places", National Journal of Otorhinolaryngology and Head & Neck Surgery, vol. 1 (10), No. 1, Apr. 2013, pp. 7-9.

Strome , "A long-term assessment of cryotherapy for treating vasomotor instability", vol. 69, No. 12, http://apps.webofknowledge.com.laneproxy.stanford.edu/OutboundServic...marked_list_candidates=1&excludeEventConfig=ExcludeIfFromFullRecPage, Dec. 1990, pp. 839-842.

Terao et al., "Cryosurgery on Postganglionic Fibers (Posterior Nasal Branches) of the Pterygopalatine Ganglion for Vasomotor Rhinitis", Acta Otolaryngol., vol. 96, 1983, pp. 139-148.

\* cited by examiner

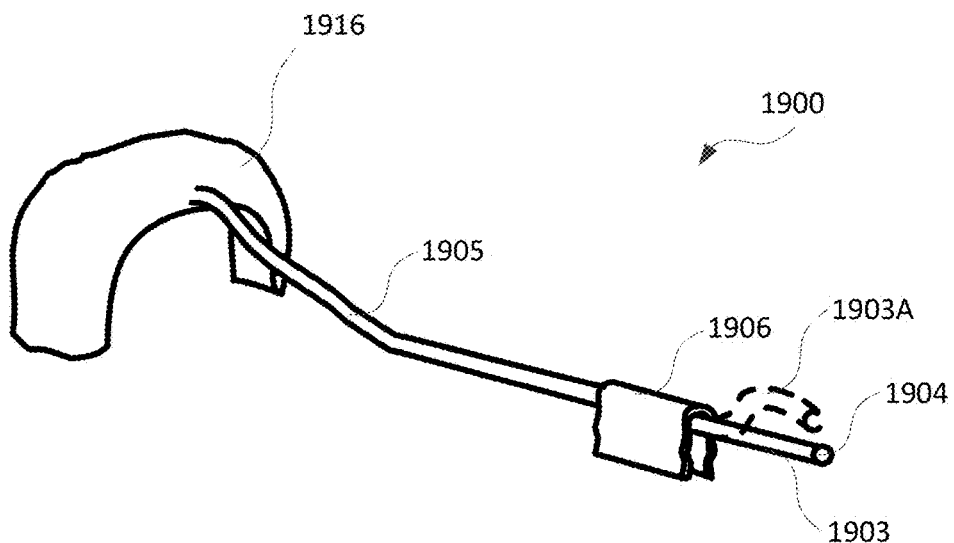
Figure 19
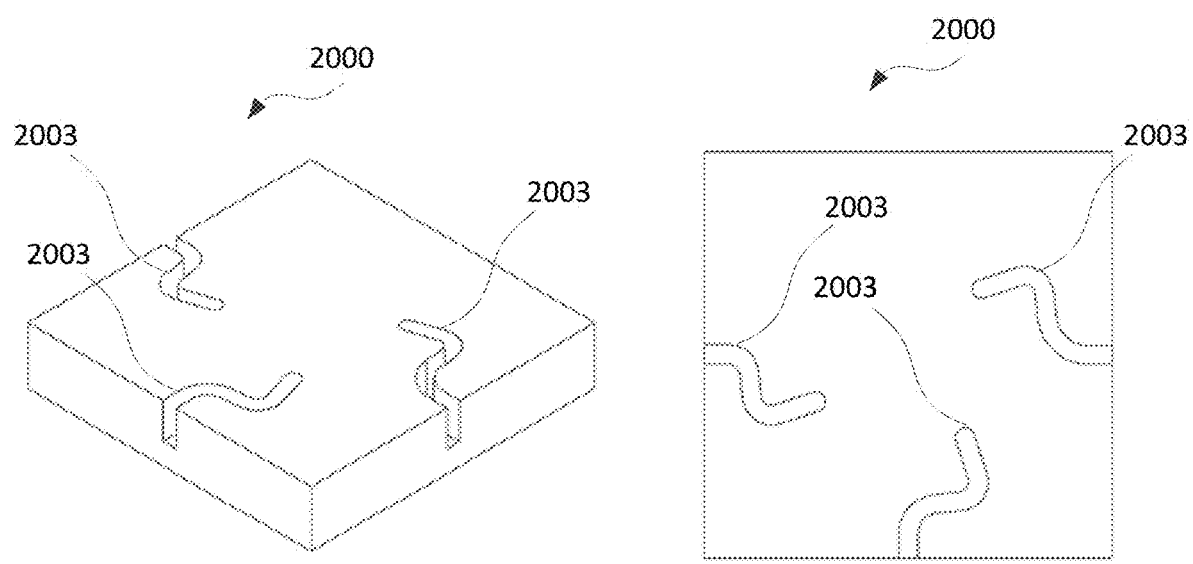
Figure 20A
Figure 20B

METHOD AND DEVICE FOR IMAGE GUIDED POST-NASAL NERVE ABLATION

This application claims the benefit of U.S. Provisional Application No. 62/294,142, filed Feb. 11, 2016, which application is incorporated herein by reference in its entirety.

The present invention relates to cryosurgical probes and their methods of use. More particularly, the present invention relates to cryosurgical probes which are configured to be advanced into a nasal cavity for treating conditions such as rhinitis.

BACKGROUND OF THE INVENTION

Field of the Invention

The major symptoms of allergic or non-allergic chronic rhinitis are sneezing, rhinorrhea, and night time coughing which are brought about by mucosal swelling, hyper-responsiveness of the sensory nerves, and an increased number and augmented responses of secretory cells in the inferior turbinates, respectively. In particular, chronic severe nasal obstruction resulting from remodeling of submucosal tissues of the inferior turbinates due to dilation of the venous sinuses or fibrosis can interfere with the quality of life (QOL).

One strategy is the surgical treatment of chronic rhinitis; that is to physically eliminate the tissue of the inferior turbinate. Removal or ablation of the mucosal tissue including the surface epithelial layer has the disadvantage of postoperative complications such as crusting and an increased infection rate. Cauterization of the surface epithelia of the inferior turbinate using electrocautery, cryosurgery, or laser yields only short-term benefits to nasal breathing. Submucosal diathermy or cryosurgery also shows only a short-term effect. Turbinectomy is thought to have the greatest effect on nasal obstruction, and slight improvement in some rhinitis patients but it is accompanied by severe adverse effects such as bleeding, crusting, and nasal dryness.

Golding-Wood, who recommended cutting the parasympathetic nerve fibers in the vidian canal to decrease the parasympathetic tone to the nasal mucosa, introduced a different approach for the treatment of hypersecretion in 1961. Various approaches to the vidian canal were subsequently developed, and the method was widely employed in the 1970s. However, the original technique was abandoned at the beginning of the 1980s because of its irreversible complications such as dry eyes.

The pterygoid canal carries both parasympathetic and sympathetic fibers, namely the vidian nerve, to the sphenopalatine ganglion. Subsequently, these autonomic fibers, which relay in the sphenopalatine ganglion, reach the nasal mucosa through the sphenopalatine foramen as the posterior nasal nerve. Resection of the posterior nasal nerve has the effect of both parasympathetic and sympathetic resection in the nasal mucosa, similar to vidian neurectomy. In addition, this procedure, in which somatic afferent innervation to the nasal mucosa is also interrupted, can be expected to reduce the hypersensitivity and axon reflexes of the nasal mucosa. The posterior nasal nerve, which follows the sphenopalatine artery and vein, arises within the sphenopalatine foramen and can be easily identified. Furthermore, selective interruption of the posterior nasal nerves has no complications, like those of vidian neurectomy, since the secretomotor supply to the lacrimal gland and the somatosensory supply to the palate are intact, and overpenetration of the pterygoid canal does not occur.

Posterior nasal neurectomy, initially developed by Kikawada in 1998 and later modified by Kawamura and Kubo, is a novel alternative method in which neural bundles are selectively cut or cauterized from the sphenopalatine foramen. Autonomic and sensory nerve fibers that pass through the foramen anatomically branch into the inferior turbinate and are distributed around the mucosal layer. Therefore, selective neurectomy at this point enables physicians to theoretically avoid surgical complications such as inhibition of lacrimal secretion.

In some cases, it may be beneficial to deliver energy to treat tissue. For example, it may be beneficial to treat rhinitis by delivering energy to the nasal cavity to ablate posterior nasal nerves. However, it can be difficult to deliver energy to the correct location without direct or indirect visualization. Current methods of delivering energy to tissue in the body require using an energy delivery device and a separate device (such as a flexible or rigid endoscope) for direct or indirect visualization. Such visualization devices are expensive, bulky, and difficult to operate simultaneously with energy delivery devices. For example, using an energy delivery device with a rigid endoscope may require the healthcare provider to use both hands, or may require a second individual to perform the procedure, which may make the procedure more time consuming and costly. Moreover, separate rigid or flexible endoscopes and existing visualization devices may not allow a healthcare provider to access far enough into the target anatomy. Accordingly, improved methods and devices are desired.

SUMMARY OF THE INVENTION

There are three nerve bundles innervating the superior, middle and inferior turbinates. The posterior, superior lateral nasal branches off of the maxillary nerve (v2) innervate the middle and superior turbinates. A branch of the greater palatine nerve innervates the inferior turbinate. Ablating these nerves leads to a decrease in or interruption of parasympathetic nerve signals that contribute to rhinorrhea in patients with allergic or vasomotor rhinitis. The objective of this invention is to design a device and method for ablating one or more of these three branches to reduce or eliminate rhinitis.

The following is the description of the embodiments that achieve the objectives of ablating the posterior nasal nerves (PNN). Any of the foregoing ablation devices can be used to ablate a single nerve branch or multiple nerve branches.

Therefore, it is an object of this invention to provide a method and apparatus configured for treating rhinitis by means of ablation of the function of one or more posterior nasal nerve(s) using optical image guidance.

In one aspect of this invention is a surgical probe configured for ablation of posterior nasal nerve function including a hollow elongated structure with a distal end, and a proximal end, an ablation element disposed in the vicinity of the distal end, and a means for connecting the ablation element to a source of an ablation agent at the proximal end. The probe further includes a camera disposed in the vicinity of the ablation element connected to an image display, whereby the distal region of the probe comprises a user articulated segment, and wherein the ablation element may comprise one of the following ablation element types: cryo-ablation, radiofrequency ablation, ultrasonic ablation, laser ablation, microwave ablation, or chemo-ablation.

In another aspect of this invention is a surgical probe configured for ablation of posterior nasal nerve function including a hollow elongated structure with a distal end, and a proximal end, an ablation element disposed in the vicinity of the distal end, and a means for connecting the ablation element to a source of an ablation agent at the proximal end. The probe further includes a camera disposed in the vicinity of the ablation element connected to an image display, whereby the distal region of the probe comprises a user articulated segment, and wherein the camera is associated with the user articulated segment.

In another aspect of this invention is a surgical probe configured for ablation of posterior nasal nerve function including a hollow elongated structure with a distal end, and a proximal end, an ablation element disposed in the vicinity of the distal end, and a means for connecting the ablation element to a source of an ablation agent at the proximal end. The probe further includes a camera disposed in the vicinity of the ablation element connected to an image display, whereby the distal region of the probe comprises a user articulated segment, and wherein the camera is associated with the articulated segment and is extendable and retractable by the user.

In another aspect of this invention is a surgical probe configured for ablation of posterior nasal nerve function including a hollow elongated structure with a distal end, and a proximal end, an ablation element disposed in the vicinity of the distal end, and a means for connecting the ablation element to a source of an ablation agent at the proximal end. The probe further includes a camera disposed in the vicinity of the ablation element connected to an image display, whereby the distal region of the probe comprises a user articulated segment, wherein the camera is associated with the articulated segment and configured for distal imaging.

In another aspect of this invention is a surgical probe configured for ablation of posterior nasal nerve function including a hollow elongated structure with a distal end, and a proximal end; an ablation element disposed in the vicinity of the distal end, and a means for connecting the ablation element to a source of an ablation agent at the proximal end. The probe further includes a camera disposed in the vicinity of the ablation element connected to an image display, whereby the distal region of the probe comprises a user articulated segment, wherein the camera is associated with the articulated segment and configured for distal imaging when in a retracted position, and configured for proximal imaging when in an extended position.

In another aspect of this invention is a surgical probe configured for ablation of posterior nasal nerve function including a hollow elongated structure with a distal end, and a proximal end; an ablation element disposed in the vicinity of the distal end, and a means for connecting the ablation element to a source of an ablation agent at the proximal end. The probe further includes a camera assembly disposed in the vicinity of the ablation element connected to an image display, whereby the distal region of the probe comprises a user articulated segment, and wherein the camera assembly is associated with the articulated segment and comprises a camera configured for distal imaging, and a second camera configured for proximal imaging.

Additional embodiments of this invention include a handpiece associated with the proximal end of the elongated structure. The hand-piece may include an internal supply of an ablation agent such as cryogen used in conjunction with a cryo-ablation element disposed in the vicinity of the distal end of the elongated structure. The hand-piece may also include a means for delivering an ablation agent to the ablation element in a controllable manner, by means of a user actuated switch or valve, or some other ablation agent delivery control means. The hand-piece may include a means for articulation of the distal end, or a means for extending or retracting a camera associated with the distal end of the elongated structure. The hand-piece may further be configured for pressing the ablation element against a lateral nasal wall proximate to a posterior nasal nerve. The pressing means may include applying a torsional or lateral force to the proximal end of the elongated structure. The hand-piece may include an indication to the user of the amount of pressing force that is being applied to the lateral nasal wall. The hand-piece may be configured with an electrical connection means for connecting the camera(s) to an imaging display. Alternatively, the ablation agent source may be external to the hand-piece, whereby the hand-piece includes a means for connection to the external ablation agent source.

Additional embodiments of the invention provide the user with a means for accomplishing additional surgical steps that are associated with surgical treatment of rhinitis. The additional surgical steps may include access to a nasal sinus, dilation of the nasal cavity, or nasal sinus, or another surgical step. The means for accomplishing said additional surgical steps may include a working channel between the proximal and distal ends of the elongated structure, whereby the working channel is configured for introducing a surgical instrument into the nasal cavity or nasal sinus.

The apparatus may be configured for delivering an anesthetic agent to the tissue in the vicinity of the target Post-Nasal Nerve prior to an ablation. The delivery means may include an injection of an anesthetic into the tissue proximate to the target Post-Nasal Nerve by means of a laterally deployable needle that is connected to a syringe. An anesthetic agent may also be delivered topically from the surface of the ablation element, wherein the surface of the ablation element may include an absorbent structure such as a fibrous structure, a hydrophilic coating, or some other means for delivering a topical anesthetic agent. The anesthetic agent may include lidocaine.

An additional aspect to this invention is a method for treating rhinitis by ablation of a posterior nasal nerve under image guidance. The method includes the steps of inserting the distal end of a posterior nasal nerve surgical probe into a nasal cavity of a patient, the posterior nasal nerve surgical probe including a hollow elongated structure with a distal end, and a proximal end, an ablation element disposed in the vicinity of the distal end, a means for connecting the ablation element to a source of an ablation agent at the proximal end, and a camera disposed in the vicinity of the ablation element connected to an image display, whereby the distal region of the probe comprises a user articulated segment, and wherein the camera is associated with the articulated segment and configured for distal or proximal imaging. The method further includes identifying the ablation target region of the lateral nasal wall with the camera, articulating the distal end of the surgical probe in a lateral direction, pressing the ablation element against the target region of the lateral nasal wall using the images from the camera, and applying the ablation agent to the lateral nasal wall to effect ablation of posterior nasal nerve function.

In another aspect, a single handheld integrated therapy and imaging device is provided. The device includes a hollow elongated cannula with a proximal portion and a distal portion, a therapeutic element coupled to the distal portion of the cannula, an imaging assembly coupled to the cannula and configured to provide visualization of the therapeutic element, and an articulating region operably coupled to the imaging assembly and configured to articulate the imaging assembly relative to an axis of insertion of the cannula into a nasal cavity.

In many embodiments of the device, the articulating region may be configured to articulate the imaging device so as to translate vertically, axially, laterally, and/or rotationally to aid in visualization of the therapeutic element. In some embodiments, the articulating region may be configured to vertically, axially, laterally, and/or rotationally translate the imaging assembly by user operation. The articulating region may be configured to vertically translate the imaging assembly so as to adjust a height of the imaging assembly relative to the insertion axis of the cannula. For example, the articulating region may be configured to adjust the height of the imaging assembly relative to the insertion axis in a range from about 1 mm to about 10 mm. The articulating region may be configured to axially translate the imaging assembly so as to adjust an axial position of the imaging assembly along the insertion axis of the cannula. For example, the articulating region may be configured to adjust the axial position in a range from about 5 mm to about 60 mm. The articulating region may be configured to laterally translate the imaging assembly so as to adjust an angular position of the imaging assembly relative to a central axis of the imaging assembly. For example, the articulating region may be configured to adjust the angular position of the imaging assembly relative to the central axis of the imaging assembly in a range from about 0 degrees to about 30 degrees. As another example, the articulating region may be configured to adjust the angular position of the imaging assembly relative to the central axis of the imaging assembly in a range from about 0 degrees to about 20 degrees while maintaining a height of the imaging assembly relative to the cannula. The articulating region may be configured to rotationally translate the imaging assembly about the insertion axis of the cannula. For example, the articulating region may be configured to rotationally translate the imaging assembly in a range from about 0 degrees to about 360 degrees about the insertion axis of the cannula, about 0 degrees to about 180 degrees about the insertion axis of the cannula, and/or 45 degrees in both directions from the insertion axis of cannula.

In many embodiments of the device, the imaging assembly may include a detector and a light element. The detector and light element may be coupled to an exterior surface of the cannula via a coupler attachment. The detector and light element may be partially within a lumen of the cannula. In some embodiments, the detector and light element are co-axially arranged. In some embodiments, the detector and light element are off-axis with respect to each other.

The arrangement of the imaging assembly relative to the therapeutic element may aid in visualization and limit the invasiveness of using the device. In some embodiments of the device, the imaging assembly is coupled to the cannula so that the articulating region is configured to articulate the imaging assembly simultaneously with the therapeutic element. In some embodiments the device may include a locking mechanism configured to maintain a fixed position of the imaging assembly relative to the therapeutic element upon articulation of the imaging assembly to a desired viewing angle or position with respect to the therapeutic element. In many embodiments, it may be desirable to arrange the imaging assembly to minimize engagement with nasal tissue. Thus, the imaging assembly may be arranged proximally from the therapeutic element so as to minimize engagement with nasal tissue. As a further example, the imaging assembly may be vertically stacked relative to the cannula so as to minimize engagement with the nasal tissue.

In many embodiments of the device, the imaging assembly may be operably coupled to a display for visualization of the therapeutic element on the display. For example, the device may include an image display disposed at the proximal end of the device and operably coupled to the imaging assembly for visualization of the therapeutic element on the display. In some embodiments, the device may include a display adaptor disposed at the proximal end of the device and operably coupled to the imaging assembly. The device may further include a display removably coupled to the display adaptor for visualization of the therapeutic element on the display. The display adaptor may include a magnetic adapter for removably coupling the display to the proximal end of the device.

In many embodiments the device may be used to provide ablation therapy. The therapeutic element may include at least one of a cryo-ablation element, a radiofrequency ablation element, an ultrasonic ablation element, a laser ablation element, a microwave ablation element, and/or a chemo-ablation element. For example, the therapeutic element may be a cryo-ablation element which is expandable from a deflated configuration to an expanded configuration. It may be desirable to keep the therapeutic element from interfering with the imaging assembly. Accordingly, the device may further include a temperature control element coupled to the imaging assembly. The temperature control element may be configured to maintain the imaging assembly within an operating temperature range during activation of the therapeutic element.

It may be desirable for the device to be held and controlled by a user. In some embodiments, the device may include a handle coupled to the proximal portion. The handle may include an articulation actuator configured to actuate the articulating region.

It may be desirable to dispose the imaging assembly on an imaging cannula separate from the working cannula of the device. In order to allow for articulation, the imaging assembly may be disposed on a flexible distal portion of an imaging cannula, the imaging cannula comprising a rigid proximal portion coupled to a handle of the device. In some embodiments, the rigid proximal portion is removably coupled to the handle of the device by a handle attachment base, the handle attachment base being configured for axial translation along the nose of the handle and rotational translation about a central axis of the nose of the handle. In some embodiments, the flexible distal portion is shapeable so as to obtain a desired viewing angle or position of the imaging assembly relative to the therapeutic element.

It may be desirable for the device to allow for delivery and/or removal of material from the nasal cavity during treatment. Accordingly the device may include at least one port configured to direct a fluid or other agent into the nasal cavity and/or suction a fluid or other agent from the nasal cavity. For example, the at least one port may be disposed on the distal portion of the cannula and fluidly coupled to a lumen of the cannula. As another example, the at least one port may be disposed on the imaging assembly.

In another aspect, a single handheld integrated cryotherapy and imaging device is provided. The device may include a hollow elongated cannula with a proximal portion and a distal portion, a cryo-ablation element coupled to the distal portion of the cannula, the cryo-ablation element being expandable from a deflated configuration to an expanded configuration, an imaging assembly coupled to the cannula and configured to provide visualization of the cryo-ablation element, and an articulating region operably coupled to the imaging assembly and configured to articulate the imaging assembly relative to an axis of insertion of the cannula into a nasal cavity.

In another aspect, a method for treating rhinitis in a tissue region within a nasal cavity is provided. The method includes inserting a distal end of an integrated therapy and imaging probe into a nasal cavity of a patient, the probe comprising a hollow elongated cannula with a proximal end and a distal end, a therapeutic element coupled to the distal end of the cannula, and an imaging assembly coupled to the cannula to provide visualization of the therapeutic element. The method further includes articulating the imaging assembly relative to an axis of insertion of the cannula into the nasal cavity until a desired viewing angle or position of the therapeutic element is obtained, and applying ablation therapy to a tissue region of a lateral nasal wall with the therapeutic element so as to treat rhinitis.

In many embodiments of the method, the imaging assembly may be articulated in various directions to obtain the desired viewing angle or position. Articulating the imaging assembly may include one of vertically translating the imaging assembly so as to adjust a height of the imaging assembly relative to the insertion axis of the cannula, axially translating the imaging assembly so as to adjust an axial position of the imaging assembly along the insertion axis of the cannula, laterally translating the imaging assembly so as to adjust an angular position of the imaging assembly relative to a central axis of the imaging assembly, or rotating the imaging assembly about the insertion axis of cannula. In some embodiments, articulating the imaging assembly includes translating the imaging assembly such that the imaging assembly is positioned distal of the therapeutic element. In some embodiments, the method further includes locking a position of the imaging assembly relative to the therapeutic element upon articulation of the imaging assembly to the desired viewing angle or position with respect to the therapeutic element.

In many embodiments, the method may further include identifying the lateral nasal wall tissue region with the imaging assembly. Identifying the lateral nasal wall tissue region with the imaging assembly may include visualizing the tissue region on a display operably coupled to the imaging assembly. For example, the display may be removably coupled to the proximal end of the probe.

In many embodiments of the method, the therapeutic element may also be articulated. For example, the method may further include articulating the therapeutic element of the probe so as to position the therapeutic element adjacent to the lateral nasal wall tissue region. This may allow for improved therapeutic effects.

It may be desirable to treat rhinitis by ablating a posterior nasal nerve. Accordingly, in many embodiments of the method, applying ablation therapy to the lateral nasal wall tissue region may include ablating at least one posterior nasal nerve within the tissue region of the lateral nasal wall with the therapeutic element.

In many embodiments, applying ablation therapy may including delivering energy to the tissue region. For example, applying ablation therapy may include delivering cryogenic energy, radio frequency energy, ultrasonic energy, light energy, microwave energy, or chemical energy to ablate the at least one posterior nasal nerve. In some embodiments, the method may include expanding the therapeutic element from a deflated configuration to an expanded configuration in contact against the lateral nasal wall tissue region. For example, expanding may include introducing a cryogenic fluid into the therapeutic element such that it is inflated from the deflated configuration into the expanded configuration against the tissue region, wherein introducing the cryogenic fluid comprises evaporating the cryogenic fluid within the therapeutic element so as to cryo-ablate the at least one posterior nasal nerve.

In order to protect the imaging assembly from the ablation energy, it may be desirable to control the temperature of the imaging assembly. For example, the imaging assembly may be maintained within an operating temperature range during ablation of the at least one posterior nasal nerve.

It may be desirable to deliver and/or remove material from the nasal cavity during treatment. Accordingly, in some embodiments, the probe includes at least one port disposed at the distal end of the probe. As an example, the port may be disposed at the distal end of the cannula and fluidly coupled to a lumen within the cannula. As another example, the port may be disposed on the imaging assembly. In some embodiments, the method further includes at least one of providing fluid or other agent into the nasal cavity using the at least one port and/or suctioning a fluid or other agent from the nasal cavity using the at least one port.

It may be desirable to dispose the imaging assembly on an imaging cannula separate from the working cannula of the device. In order to allow for articulation, the imaging assembly may be disposed on a flexible distal portion of an imaging cannula, the imaging cannula comprising a rigid proximal portion coupled to a handle of the device. In some embodiments, the rigid proximal portion is removably coupled to the handle of the device by a handle attachment base, and the method further includes at least one of axially translating the handle attachment base along the nose of the handle so as to axially translate the imaging assembly, and/or rotationally translating the handle attachment base about a central axis of the nose of the handle so as to rotationally translate the imaging assembly about the insertion axis of cannula. In some embodiments, articulating the imaging assembly comprises shaping, using a template, the flexible distal portion of the imaging lumen prior to inserting the distal end of the integrated therapy and imaging probe into the nasal cavity of the patient.

The above brief summary presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented below.

For a fuller understanding of the nature and advantages of the present invention, reference should be made to the ensuing detailed description and accompanying drawings.

BRIEF DESCRIPTION OF THE DRAWINGS

FIG. 19 shows a perspective view of an imaging attachment with a malleable distal portion, according to embodiments of the invention.

FIGS. 20A and 20B show views of a template used to shape the malleable distal portion of the imaging attachment of FIG. 19, according to embodiments of the invention.

DETAILED DESCRIPTION OF THE INVENTION

Figure 1:
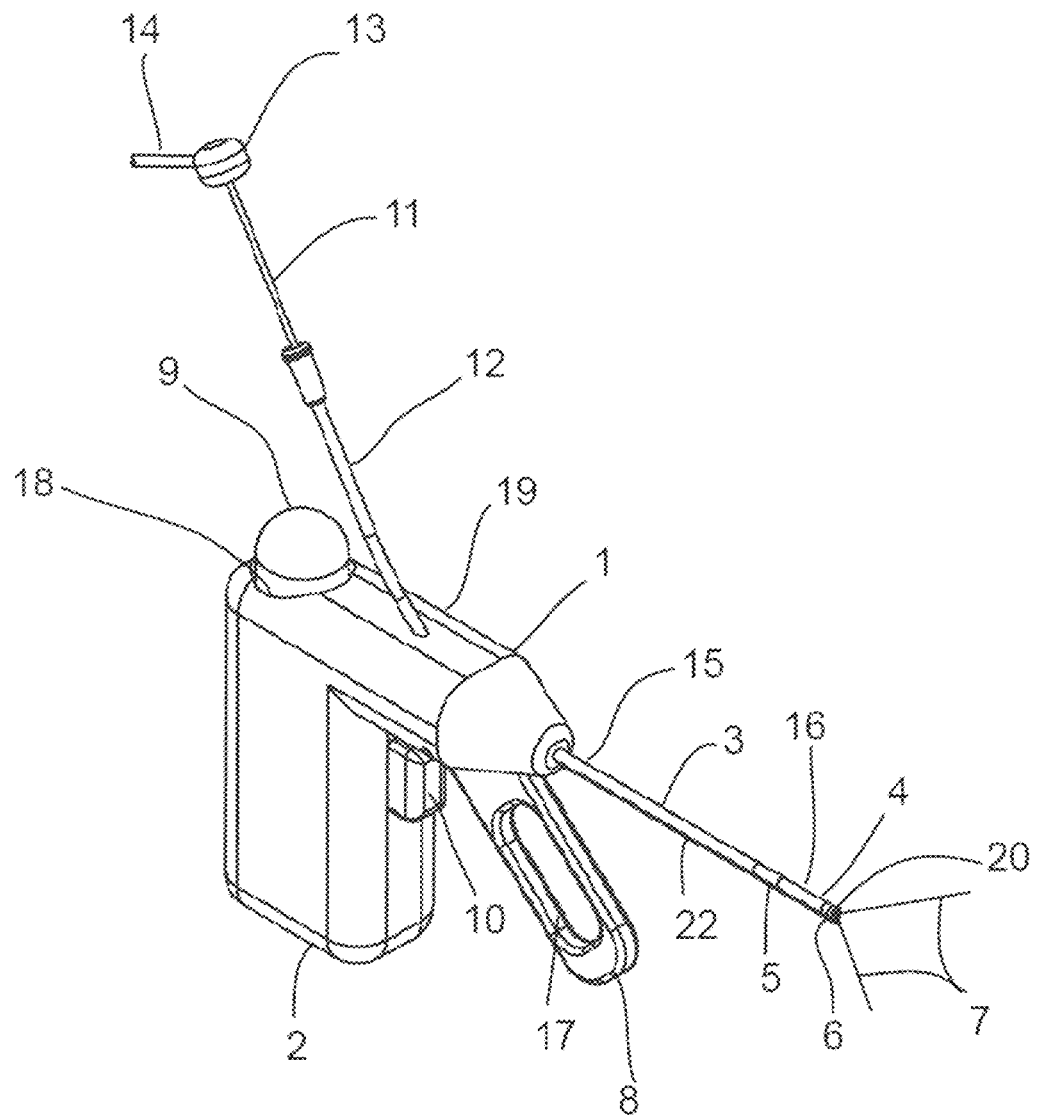
FIG. 1 is a schematic illustration of a surgical ablation probe configured for ablation of posterior nasal nerve function.

FIG. 1 is a schematic illustration of surgical ablation probe 1 configured for ablation of posterior nasal nerve function. As depicted in the figures, surgical ablation probe 1, and its alternative embodiments are cryo-ablation probes. However, alternative ablation and therapeutic modalities, including radiofrequency, laser, microwave, ultrasonic, and chemo-ablation remain within the scope of this invention. Surgical ablation probe 1 comprises handle assembly 2, probe shaft 3, and camera assembly 6. Handle assembly 2 comprises handle housing 19, cryogen cartridge receptacle 18, cryogen cartridge 9, cryogen control trigger 10, distal segment actuator lever 8 with finger grip 17, and camera tube 12. Probe shaft 3 comprises proximal end 15, distal end 16, cryo-ablation element 4, distal articulated segment 5, proximal segment 21, and camera channel 22. Camera assembly 6 comprises camera head 20, camera shaft 11, camera hub 13, camera electrical cable 14, and camera field of view 7 is depicted in the distal direction. Probe shaft 3 is between approximately 3 mm and 5 mm in diameter, and between approximately 40 mm and 100 mm long. Cryo-ablation element 4 is disposed in the vicinity of distal end 16 of probe shaft 3, and is associated with articulated segment 5. Distal articulated segment 5 is between approximately 8 mm to 20 mm long and comprises distal end 16. Camera head 20 may include a miniature CMOS camera and light source, and is mounted on the distal end of camera shaft 11. As depicted, camera field of view 7 is in the distal direction. Cameras with integrated light source are manufactured by Awaiba, which are described in detail at awaiba.com. Camera shaft 11 comprises a hollow flexible tube, which may be metallic, or a suitable plastic such polyimide. Camera shaft 11 houses wires that connect the camera and light source within camera housing 20 to an imaging console, not shown, through camera hub 13, and camera cable 14. Camera assembly 6, and alternate embodiments will be described in further detail below. Probe shaft 3 also comprises camera lumen 22, which is contiguous with camera tube 12. Cryogen cartridge 9 comprises a cryogen supply which may be in liquid or gas form. Cryogen cartridge is in fluidic communication with cryo-ablation element 4, through a cryogen control valve associated with cryogen trigger 10. When cryogen trigger 10 is depressed by the user, cryogen flows to cryo-ablation element 4. When cryogen trigger 10 is released by the user cryogen flow terminates. Exhausted cryogen from cryo-ablation element is vented to the room through the interior of probe shaft 3, and a port in handle assembly 2, not shown.

Figure 2A:
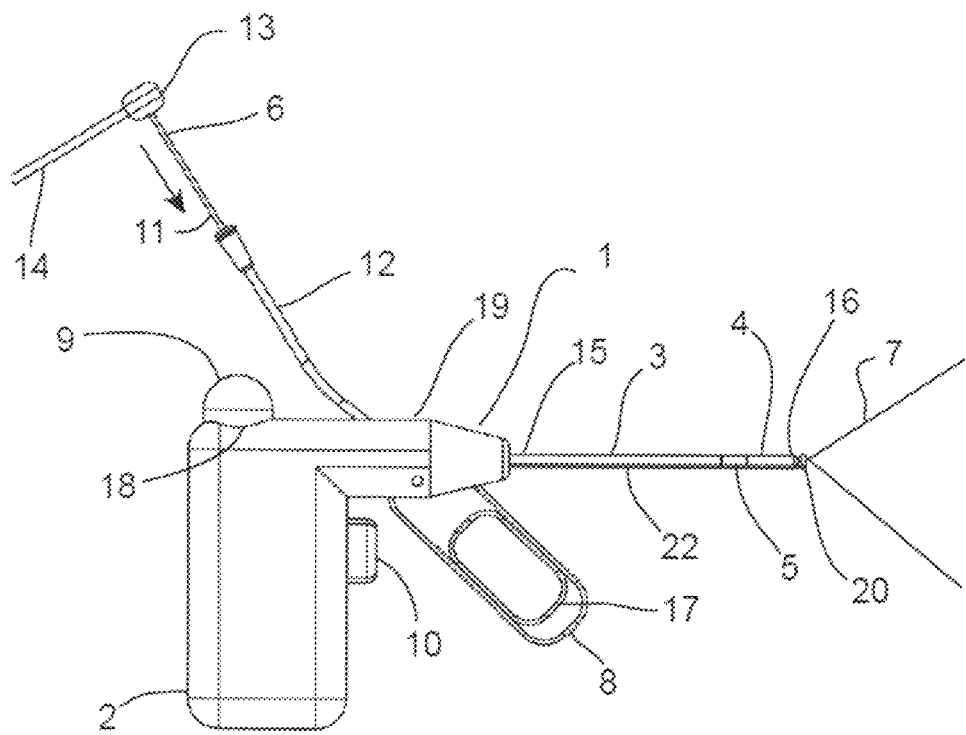
FIG. 2A is a side view schematic illustration of a surgical probe configured for ablation of posterior nasal nerve function with the articulated segment in an axial configuration, with the camera retracted.
Figure 2B:
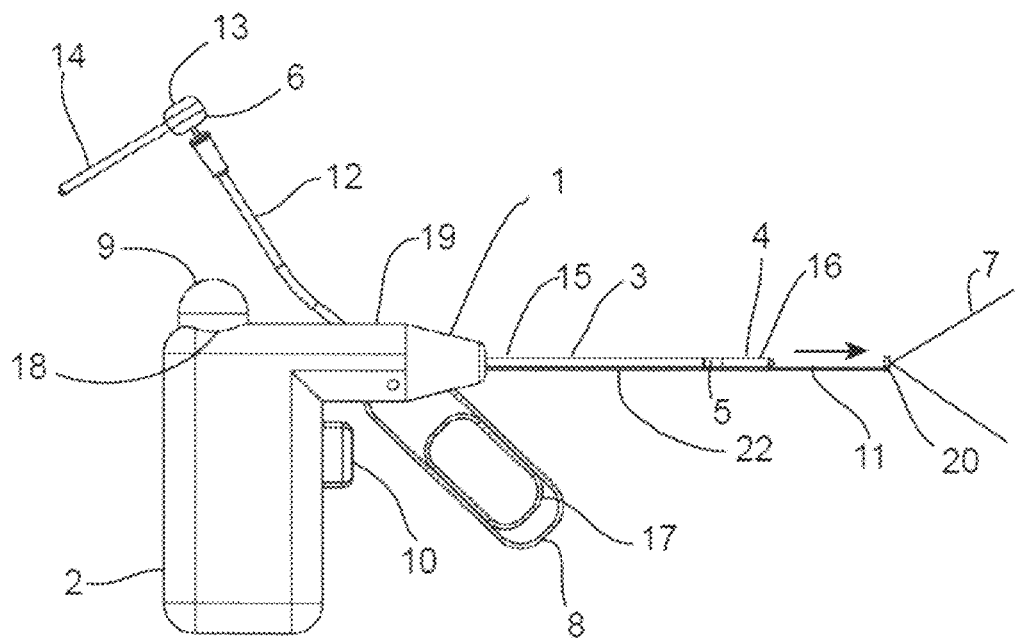
FIG. 2B is a side view schematic illustration of a surgical probe configured for ablation of posterior nasal nerve function with the articulated segment in an axial configuration, with the camera extended.

FIG. 2A is a side view schematic illustration of surgical probe 1 with distal articulated segment 5 in an axial configuration with camera head 20 retracted. FIG. 2B is a side view schematic illustration of surgical probe 1 with distal articulated segment 5 in an axial configuration, with camera head 20 extended. Camera assembly 6 comprises camera head 20, camera shaft 11, camera hub 13, camera cable 14, and an electrical connector, not shown, configured for electrical connection to an imaging display, also not shown. Camera shaft 11 is in a slidable relationship with camera tube 12, and camera lumen 22 of probe shaft 3. As depicted, camera head 20 is extended by sliding camera shaft 11 in the distal direction, and retraction of camera head 20 is accomplished by sliding camera shaft 11 in the proximal direction.

Figure 3A:
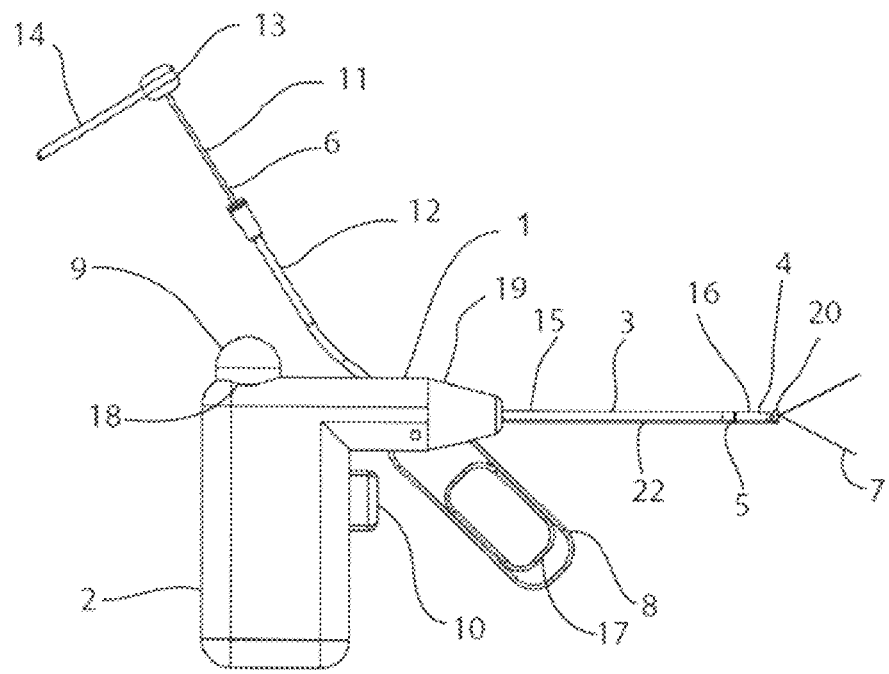
FIG. 3A is a side view schematic illustration of a surgical probe configured for ablation of posterior nasal nerve function with the articulated segment in an axial configuration, with the camera retracted.
Figure 3B:
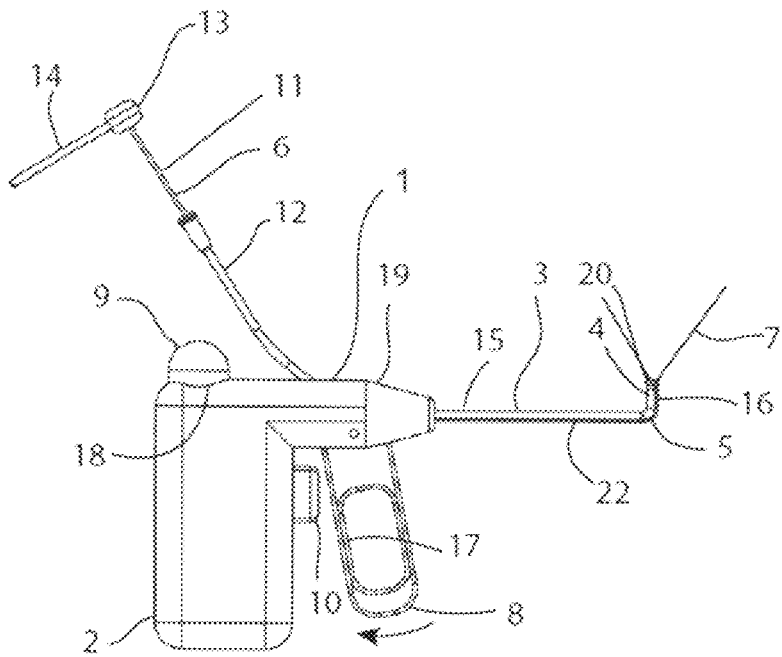
FIG. 3B is a side view schematic illustration of a surgical probe configured for ablation of posterior nasal nerve function with the articulated segment in a lateral configuration with the camera retracted.
Figure 3C:
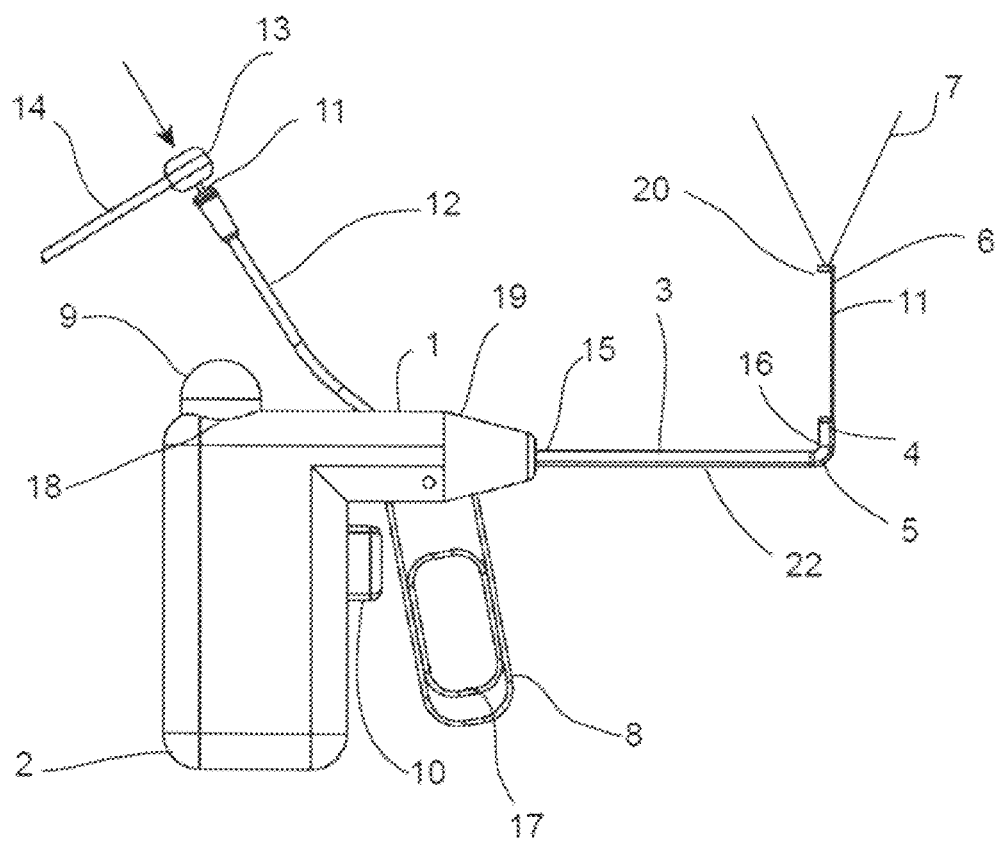
FIG. 3C is a side view schematic illustration of a surgical probe configured for ablation of posterior nasal nerve function with the articulated segment in a lateral configuration with the camera extended.

FIG. 3A is a side view schematic illustration of surgical probe 1 configured for ablation of posterior nasal nerve function with articulated segment 5 and cryo-ablation element 4 in an axial configuration, with the camera assembly 6 retracted into its proximal most position. FIG. 3B is a side view schematic illustration of surgical probe 1 with articulated segment 5 and cryo-ablation element in a lateral configuration with camera assembly 4 retracted in its proximal most position. FIG. 3C is a side view schematic illustration of surgical probe 1 with articulated segment 5 in a lateral configuration and with camera assembly 4 extended to its distal most position. Distal segment actuator lever 8 controls the position of distal articulated segment 5 and cryo-ablation element 4. When distal segment actuator lever 8 is in its forward position as depicted in FIG. 3A, distal articulated segment 5 and cryo-ablation element 4 is in an axial configuration as shown. When distal segment actuator lever 8 is pulled in the proximal direction, distal articulated segment 5 and cryo-ablation element are deflected into a lateral or non-axial position as shown in FIGS. 3B and 3C. Although illustratively referred to herein as actuator lever 8, it will be understood that other mechanisms may be employed for creating a distal articulated segment as depicted here, including the use of eccentrically anchored pull wires. The combination of articulated distal segment 5 and associated camera assembly 6 provides the user with a means of endoscopically examining a nasal cavity in a distal axial and distal lateral directions, and the extension of camera assembly 6 as depicted allows the user to endoscopically examine nasal sinuses from the nasal cavity. Probe shaft 3 is configurable to be torsionally stiff to provide a rotational manipulation in addition to the lateral manipulation as described. This allows camera head 20 to be aimed over a spherical arc, and also provides the user the means to press cry-ablation element against the lateral nasal wall using torsional force.

Figure 4:
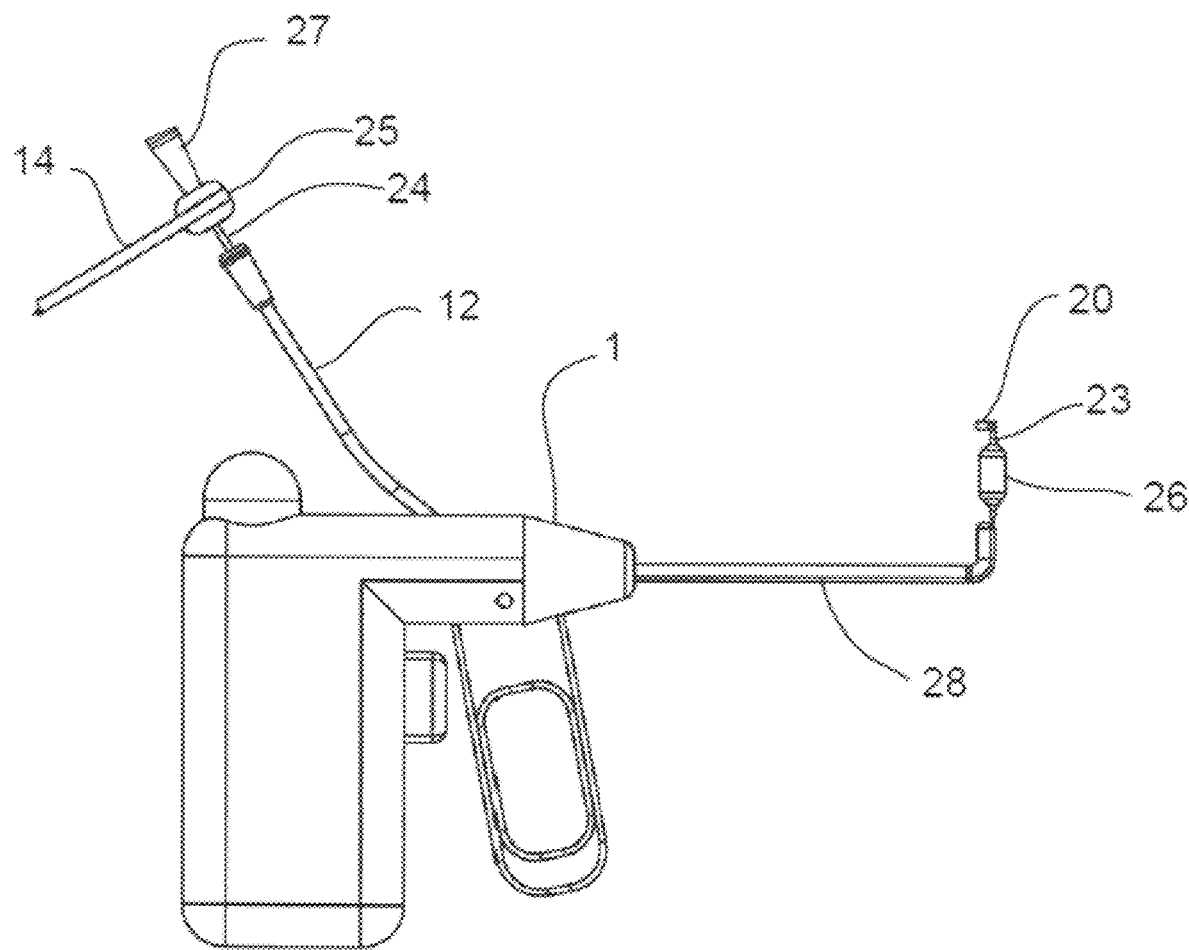
FIG. 4 is a side view schematic illustration of surgical probe configured for ablation of posterior nasal nerve function showing a sinuplasty balloon mounted on the camera shaft proximal to the camera.

FIG. 4 is a side view schematic illustration of surgical probe 1 configured for ablation of posterior nasal nerve function showing a sinuplasty balloon 26 mounted on camera shaft 24 proximal to camera head 20 of camera/balloon assembly 23. In the embodiment depicted here, posterior nasal nerve ablation probe 1 is substantially identical in form and function as previously described. In the embodiment depicted in this figure, a sinuplasty functionality is added, by adding a dilatation balloon to the distal camera shaft. Sinuplasty refers to dilatation of the os of a nasal cavity to facilitate sinus drainage. In this embodiment camera/balloon assembly 23 comprises camera head 20, which retains the form and function as previously described, camera shaft 24, which includes a balloon inflation lumen, not shown, and the electrical wires connected to the CMOS camera, not shown. Camera hub 25 comprises a female luer fitting, which is in fluidic communication with the balloon inflation lumen, and electrical cable 14 and an electrical connector, not shown. Dilatation balloon 26 is substantially similar to dilatation balloons used in angioplasty procedure. Those skilled in the art of surgical dilatation balloon design and manufacture are familiar with the means for incorporating a dilatation balloon as depicted; therefore, no further description of the dilatation balloon is warranted. As depicted, camera head 20 is extended, and balloon 26 is inflated. During insertion of the probe into the nasal cavity, camera head 20, and camera shaft 24 are retracted, and balloon 26 is deflated and resides within camera shaft lumen 28. To inflate balloon 26, a syringed is connected to female luer fitting 27, and the syringe is used to inflate balloon 27. Balloon 27 may be between approximately 3 to 10 mm in diameter when fully inflated, and may have a functional length between approximately 10 mm and 20 mm. The camera is used to located the os of the sinus, and camera head 20 is inserted through the os of the sinus, and balloon 26 is placed into a straddling position within the os, and then inflated to dilate the os. Balloon 26 is then deflated, and camera head 20 is withdrawn from the sinus.

Figure 5A:
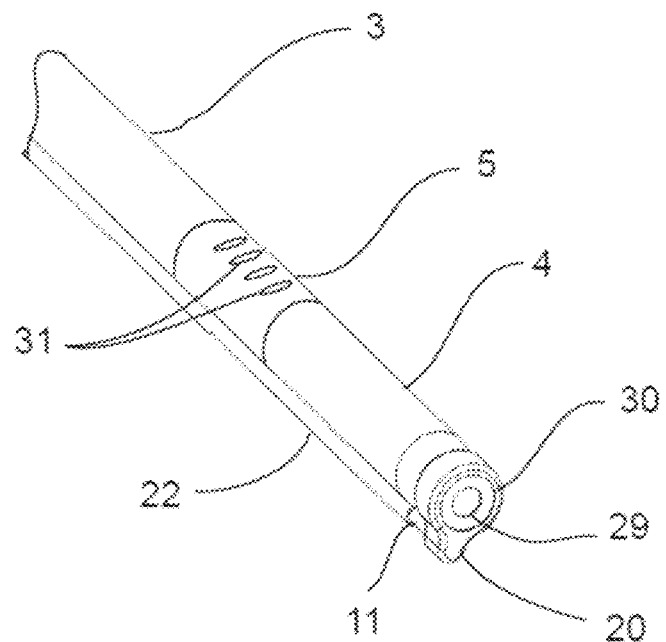
FIG. 5A is a schematic illustration of the distal end of a surgical probe configured for ablation of posterior nasal nerve function with the articulated segment in an axial configuration with the camera retracted.
Figure 5B:
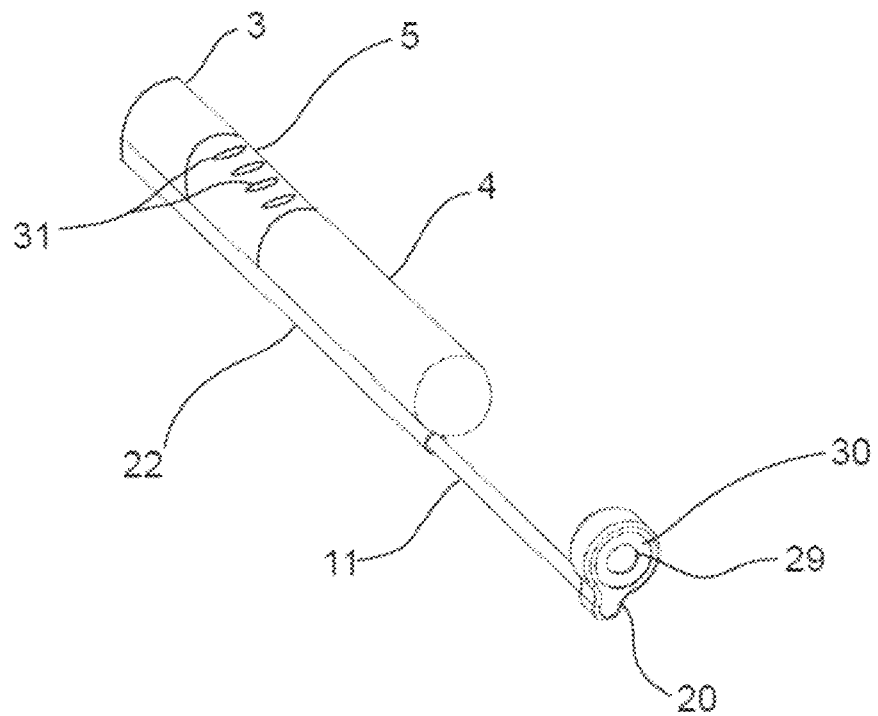
FIG. 5B is a schematic illustration of the distal end of a surgical probe configured for ablation of posterior nasal nerve function with the articulated segment in an axial configuration with the camera extended.

FIG. 5A is a schematic illustration of the distal end of a surgical probe 1 configured for ablation of posterior nasal nerve function with distal articulated segment 5 and cryo-ablation element 4 in an axial configuration with camera assembly 6 retracted. FIG. 5B is a schematic illustration of the distal end of surgical probe 1 with distal articulated segment 5 and cryo-ablation element 4 in an axial configuration with camera assembly 6 extended. Camera objective 29, and camera light source 30 is depicted. Also depicted are relief slits 31 in the wall of distal articulated segment 5 which are oriented on the side of lateral deflection. Relief slits 31 facilitate lateral deflection with a relatively short radius by removing shaft material on the inner bend radius. Camera shaft lumen 22 may comprise coiled wire reinforcement, not shown, in the vicinity of distal articulated segment 5 to prevent kinking.

Figure 6A:
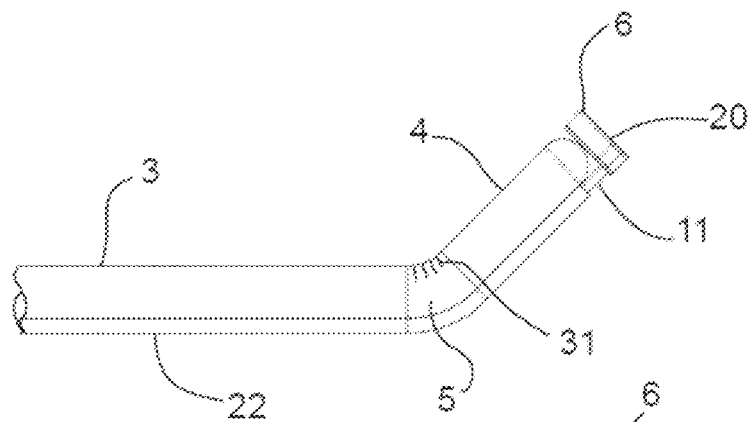
FIG. 6A is a schematic illustration of the distal end of a surgical probe configured for ablation of posterior nasal nerve function with the articulated segment in a lateral configuration at approximately 45 degrees with the camera retracted.
Figure 6B:
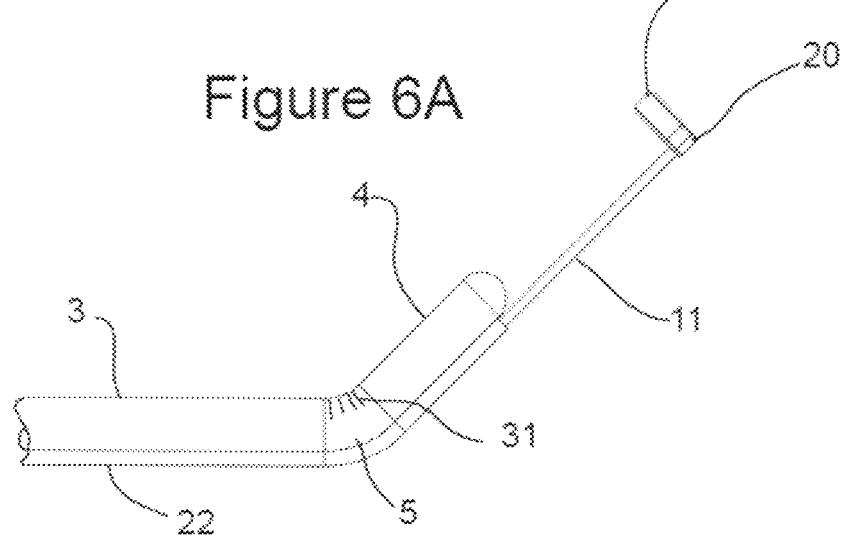
FIG. 6B is a schematic illustration of the distal end of a surgical probe configured for ablation of posterior nasal nerve function with the articulated segment in a lateral configuration at approximately 45 degrees with the camera extended.
Figure 6C:
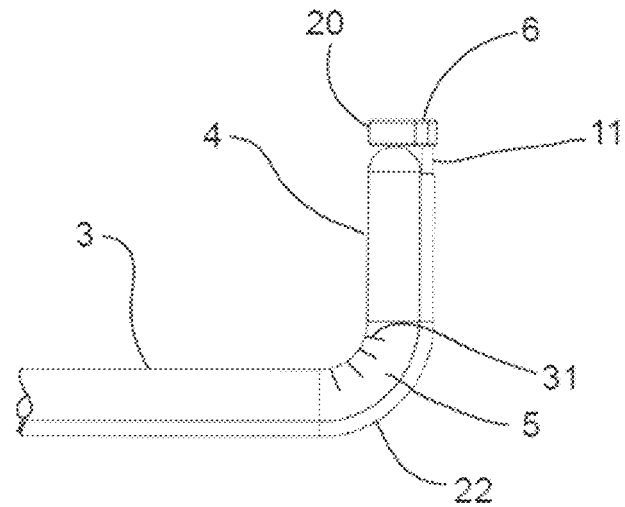
FIG. 6C is a schematic illustration of the distal end of a surgical probe configured for ablation of posterior nasal nerve function with the articulated segment in a lateral configuration at approximately 90 degrees with the camera retracted.
Figure 6D:
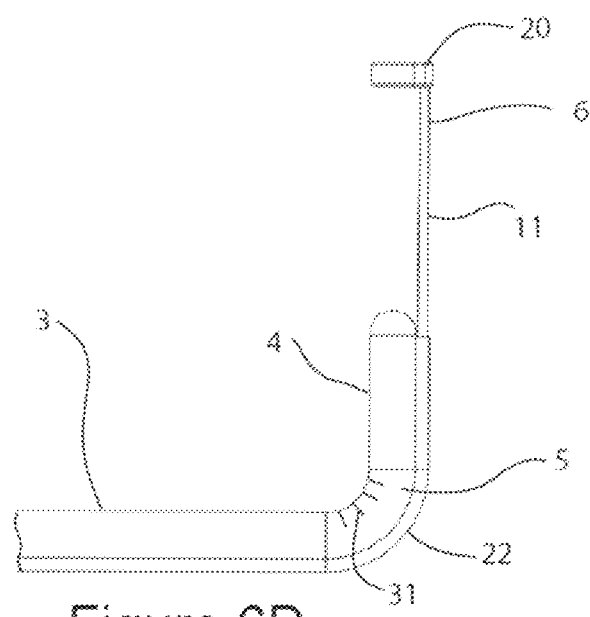
FIG. 6D is a schematic illustration of the distal end of a surgical probe configured for ablation of posterior nasal nerve function with the articulated segment in a lateral configuration at approximately 90 degrees with the camera extended.
Figure 6E:
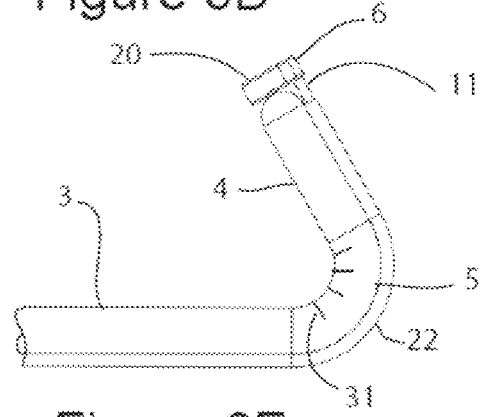
FIG. 6E is a schematic illustration of the distal end of a surgical probe configured for ablation of posterior nasal nerve function with the articulated segment in a lateral configuration at approximately 120 degrees with the camera retracted.
Figure 6F:
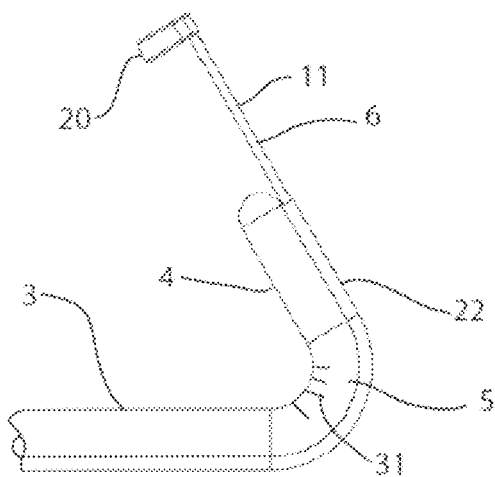
FIG. 6F is a schematic illustration of the distal end of a surgical probe configured for ablation of posterior nasal nerve function with the articulated segment in a lateral configuration at approximately 120 degrees with the camera extended.

FIG. 6A is a schematic illustration of the distal end of a surgical probe 1 configured for ablation of posterior nasal nerve function with distal articulated segment 5 and cryo-ablation element 4 in a lateral configuration at approximately 45 degrees with the camera assembly 6 retracted. FIG. 6B is a schematic illustration of the distal articulated segment 5 and cryo-ablation element 4 in a lateral configuration at approximately 45 degrees with camera assembly 6 extended. FIG. 6C is a schematic illustration of the distal end of a surgical probe 1 with distal articulated segment 5 and cryo-ablation element 4 in a lateral configuration at approximately 90 degrees with camera assembly 6 retracted. FIG. 6D is a schematic illustration of the distal end of a surgical probe 1 with distal articulated segment 5 and cryo-ablation element 4 in a lateral configuration at approximately 90 degrees with camera assembly 6 extended. FIG. 6E is a schematic illustration of the distal end of surgical probe 1 with distal articulated segment 5 and cryo-ablation element 4 in a lateral configuration at approximately 120 degrees with camera assembly 6 retracted. FIG. 6F is a schematic illustration of the distal end of a surgical probe with distal articulated segment 5 and cryo-ablation element 4 in a lateral configuration at approximately 120 degrees with camera assembly 6 extended. FIG. 6A through 6F are illustrative of the range of motion of distal articulated segment 5, cryo-ablation element 4 and camera assembly 6.

Figure 7A:
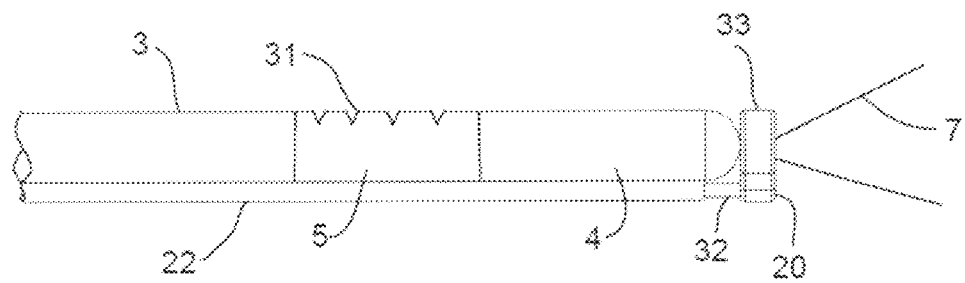
FIG. 7A is a schematic illustration of the distal end of an alternative embodiment of a surgical probe configured for ablation of posterior nasal nerve function with the articulated segment in an axial configuration and a back looking camera retracted.
Figure 7B:
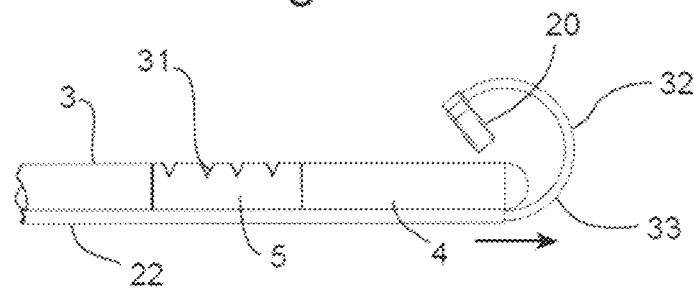
FIG. 7B is a schematic illustration of the distal end of an alternative embodiment of a surgical probe configured for ablation of posterior nasal nerve function with the articulated segment in an axial configuration and a back looking camera in its initial stage of extension.
Figure 7C:
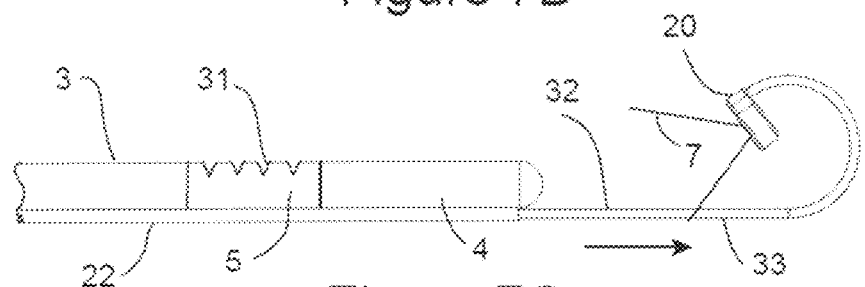
FIG. 7C is a schematic illustration of the distal end of an alternative embodiment of a surgical probe configured for ablation of posterior nasal nerve function with the articulated segment in an axial configuration and a back looking camera in its fully extended position.
Figure 7D:
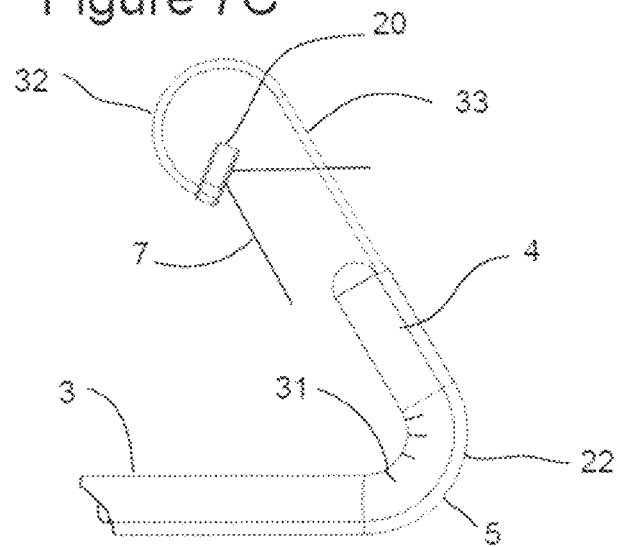
FIG. 7D is a schematic illustration of the distal end of an alternative embodiment of a surgical probe configured for ablation of posterior nasal nerve function with the articulated segment in an approximately 120 degree lateral configuration, and a back looking camera in its fully extended position, which is the normal ablation configuration.

FIG. 7A is a schematic illustration of the distal end of an alternative embodiment of a surgical probe configured for ablation of posterior nasal nerve function with distal articulated segment 5 in an axial configuration with back looking camera assembly 33 retracted. FIG. 7B is a schematic illustration of the distal end of the alternative embodiment with distal articulated segment 5 in an axial configuration and back looking camera assembly 33 in its initial stage of extension. FIG. 7C is a schematic illustration of the distal end of the alternative embodiment with distal articulated segment 5 in an axial configuration and back looking camera assembly 33 in its fully extended position. FIG. 7D is a schematic illustration of the distal end of the alternative embodiment with distal articulated segment 5 in an approximately 120 degree lateral configuration, and back looking camera assembly 33 in its fully extended position, which is the normal ablation configuration. Back looking camera assembly 33 provides the user with a means for confirming the correct placement of cryo-ablation element 4 against the lateral nasal wall proximate to a target Post Nasal Nerve. Back looking camera assembly 33 comprises camera head 20, as previously described, curved camera shaft 32, and camera hub 13, and camera cable 14, not shown, but previously described. Curved camera shaft 32 has pre-formed curve as shown. Curved camera shaft may be fabricated using a super elastic metal alloy such Nitinol® in the form of a hypotube. Those skilled in the art of super-elastic metallurgy are familiar with means for creating the pre-formed curve as shown; therefore, no further description is warranted.

Figure 8:
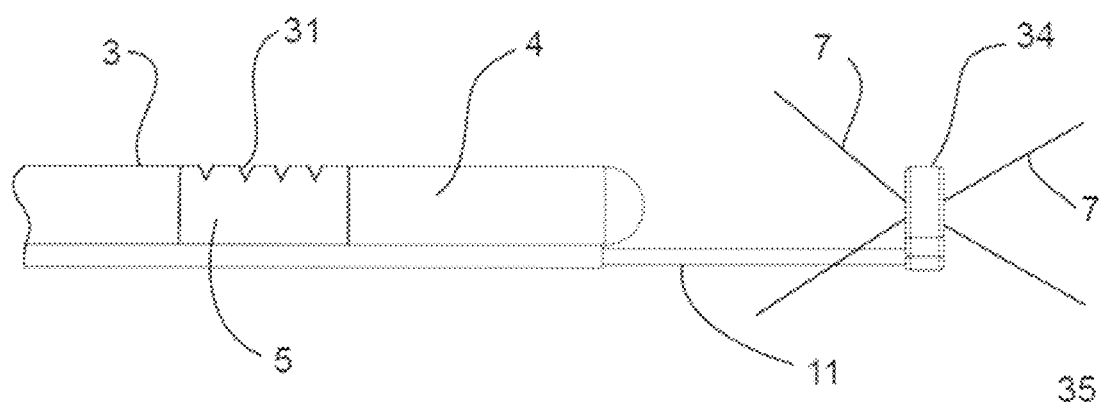
FIG. 8 is a schematic illustration of the distal end of an alternative embodiment of a surgical probe configured for ablation of posterior nasal nerve function with the articulated segment in an axial configuration and a camera assembly comprising a distal looking camera and a proximal looking camera in its extended position.

FIG. 8 is a schematic illustration of the distal end of an alternative embodiment of a surgical probe configured for ablation of posterior nasal nerve function with distal articulated segment 5 in an axial configuration and dual camera assembly 34 comprising a distal looking camera and a proximal looking camera in its extended position, as illustrated by camera field of views 7. Dual camera assembly 34 comprises dual camera head 35, camera shaft 11, camera hub 13 and camera cable 14, not shown but previously described. Dual camera head 35 comprises a forward-looking CMOS camera and light source as previously described, and a second back-looking CMOS camera and light source.

Figure 9:
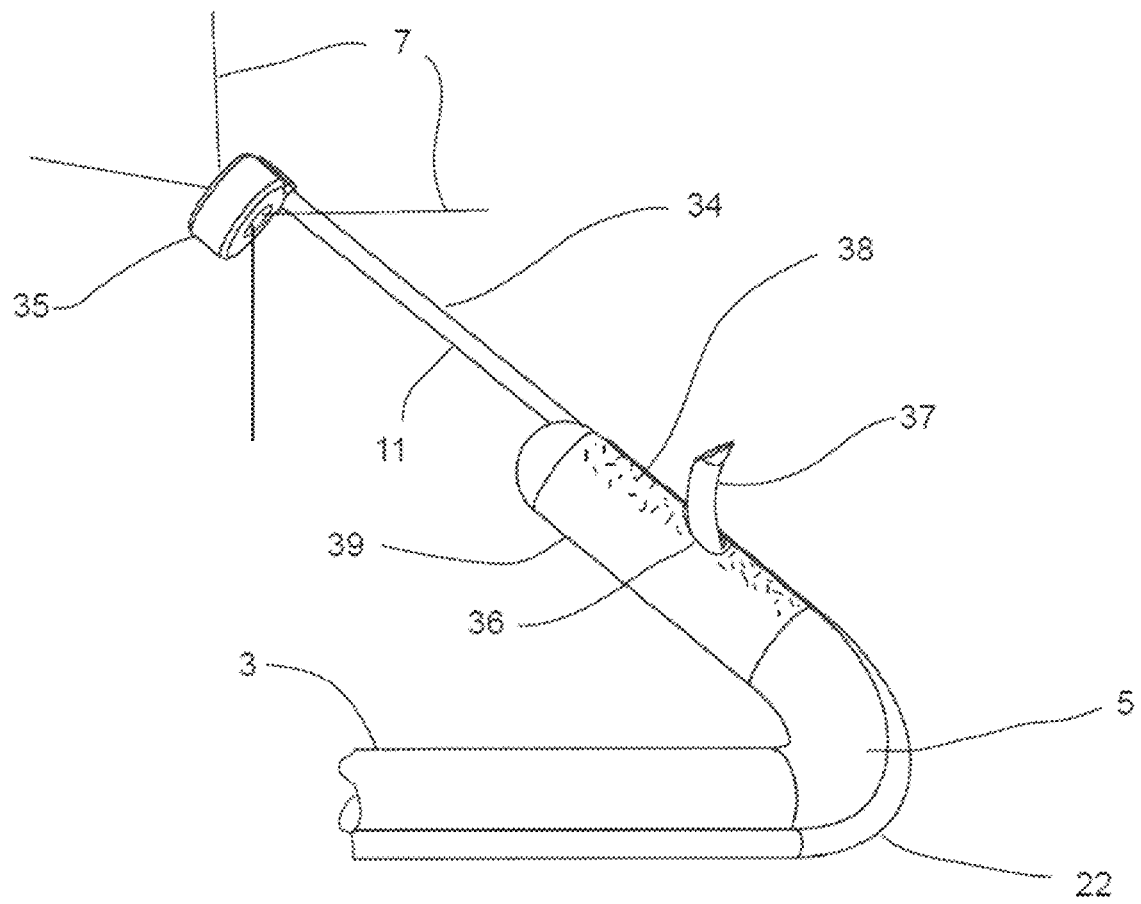
FIG. 9 is a schematic illustration of the distal end of an alternative embodiment of a surgical probe configured for ablation of posterior nasal nerve function with the articulated segment in an approximately 120 degree lateral configuration, a camera in its extended position and a laterally deployed needle for anesthetic injection into the posterior nasal nerve ablation target region of the lateral nasal wall.

FIG. 9 is a schematic illustration of the distal end of an alternative embodiment of a surgical probe configured for ablation of posterior nasal nerve function comprising cryo-ablation element 39 configured with lateral injection needle 37, lateral fenestration 36, and topical anesthetic delivery surface 38. As depicted distal articulated segment 5 is in an approximately 120 degree lateral configuration, dual camera assembly 34 camera in its fully extended position and lateral injection needle 37 is deployed for anesthetic injection into the posterior nasal nerve ablation target region of the lateral nasal wall. Topical anesthetic delivery surface 38 is configured for applying a topical anesthetic to the lateral nasal wall proximate to the target posterior nasal nerve, in order to numb the region prior to injection of the anesthetic through lateral needle 37. Lateral needle 37 is a hypotube, which may be fabricated from a super-elastic metal, such as Nitinol®. Lateral needle 37 is in fluidic communication with a proximal syringe, not shown, and is configured with a proximal needle deployment mechanism, not shown. Those skilled in the art of surgical needle probes are familiar with the means for creating a deployable needle as described; therefore no further description is warranted. Topical anesthetic delivery surface 38 may comprises an anesthetic carrying means such as a hydrophilic coating, or a foam or fibrous absorbable material that can absorb a topical anesthetic and deliver the anesthetic to the surface of a nasal wall by contact. Topical anesthetic delivery surface 38 may comprise an abrasive material configured to abrade the nasal wall to enhance the effectiveness of the topical anesthetic. The abrasive material may comprise crystalline lidocaine, or similar anesthetic material.

Figure 10:
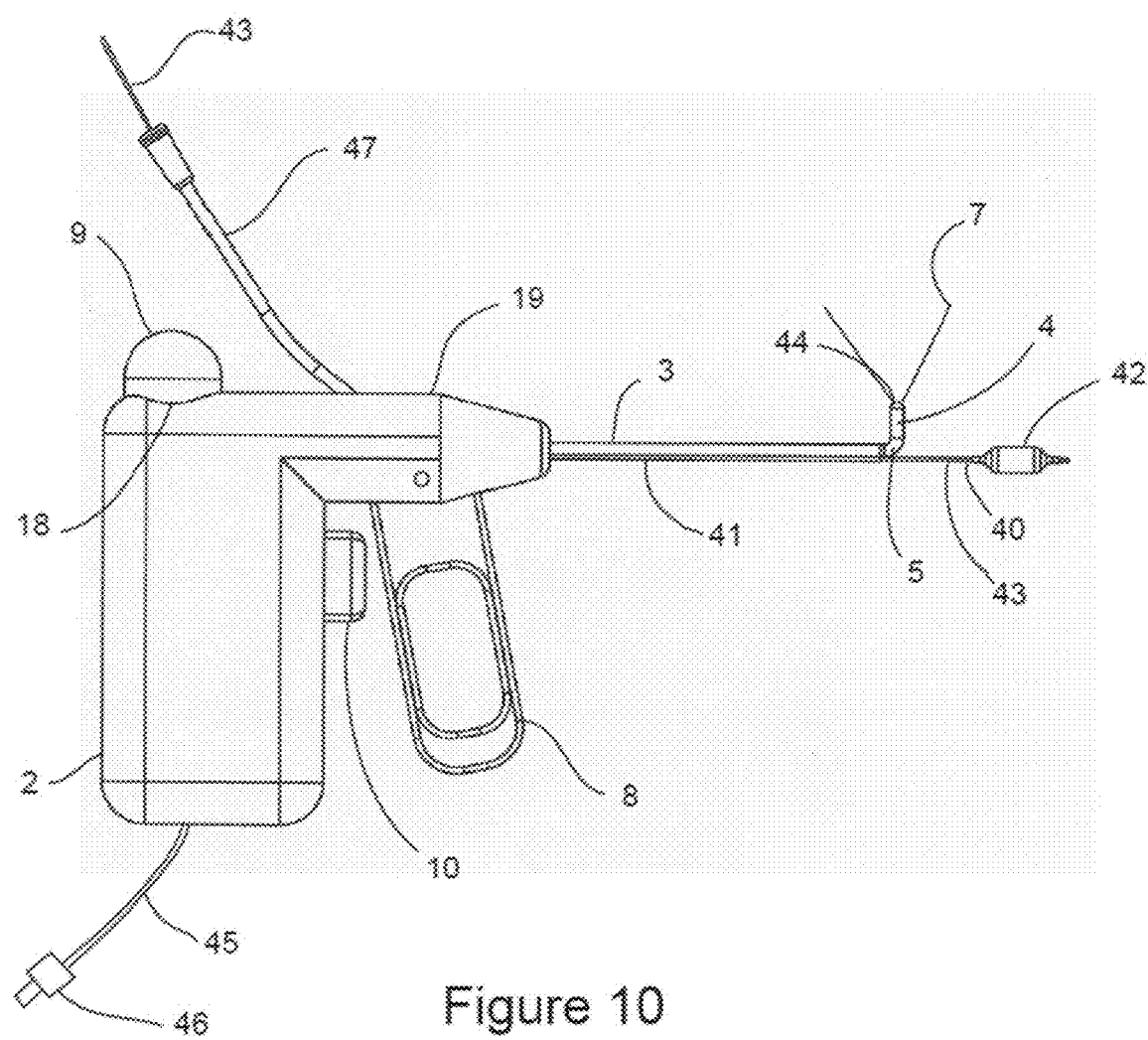
FIG. 10 is a schematic illustration of the distal end of an alternative embodiment of a surgical probe configured for ablation of posterior nasal nerve function with the articulated segment in a 90 degree lateral configuration, a camera mounted at the distal end of the ablation element, and a sinuplasty balloon catheter extending beyond the distal end of a working channel.

FIG. 10 is a schematic illustration of the distal end of an alternative embodiment of a surgical probe configured for ablation of posterior nasal nerve function comprising distal camera 44 mounted at the distal end of cryo-ablation element 4, and working channel 41, which is configured to introduce surgical instruments into the nasal cavity under image guidance. As depicted, balloon catheter 40 is inserted into working 41, with balloon 42, and the distal end of catheter shaft 43 extending beyond the distal end of working channel 41. The proximal end of catheter shaft is depicted entering working channel 41 through working channel tube 47. Distal camera 44 is connected to an image display, not shown by electrical cable 45, and electrical connector 46. As depicted, distal articulated segment 5 is in a 90 degree lateral configuration. The range of motion of distal articulated segment 5 is substantially the same as previously describe and between approximately zero and 120 degrees. Working channel 41 may be configured for use with catheters and probes between approximately 3 and 6 French.

Figure 11A:
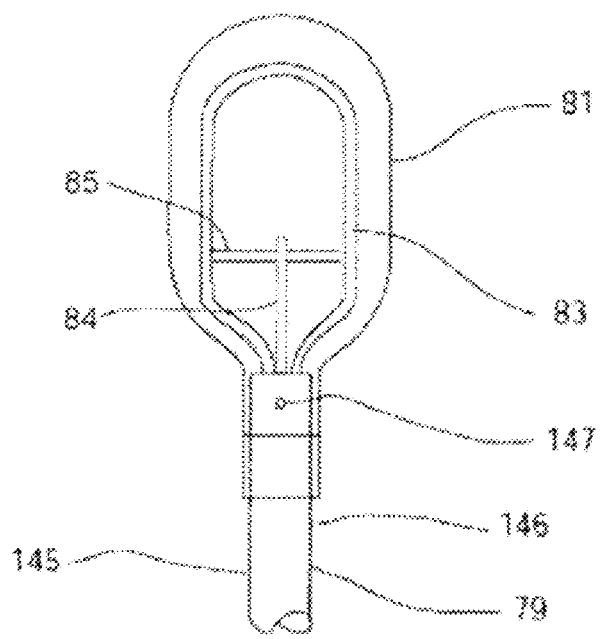
FIGS. 11A-11D show views of a therapeutic element at the distal end of a surgical probe, according to embodiments of the invention.

As described above, a number of therapeutic modalities are within the scope of the present invention. Additional therapeutic modalities, including cryogenic ablation elements, are described in U.S. Patent Application Publication No. 2015/0164571, titled "Apparatus And Methods for Treating Rhinitis," which application is incorporated herein by reference in its entirety. FIGS. 11A-11D show views of one such alternate embodiment of a cryogenic ablation element, according to embodiments of the invention. In particular, the side view of FIG. 11A shows a structure or member 83 which is formed into a looped and elongated structure having arcuate edges for presenting an atraumatic surface. Rather than being formed as a spring like structure, the structure 83 may be formed of a relatively rigid wire or member instead which maintains its configuration when pressed against a tissue surface. Structure 83 may form a continuous structure which defines an opening there through such as a looped or elongated and looped member which is open through the loop. The structure 83 may be contained entirely within the expandable structure 81 which may be formed to have a predefined shape which is distensible or non-distensible when inflated by the cryogen. Moreover, the expandable structure 81 may be formed to surround the structure 83 entirely without being supported by or attached to the structure 83 itself. Such a structure 83 may provide a configuration which presents a low-profile as the device is advanced into and through the nasal cavity and between the nasal turbinate tissues. Yet because of the relatively flattened shape and rigidity and integrity of the structure 83, the structure 83 may be used to manipulate, move, or otherwise part the tissues of the nasal cavity without having to rely upon the expandable structure 81. Additionally, the low-profile enables the structure 83 to be positioned desirably within the narrowed confines of, e.g., the cul-de-sac in proximity to the posterior nasal nerves (as shown by cul-de-sac 13 shown in FIG. 1 of previously incorporated U.S. Patent Application Publication No. 2015/0164571). When the expandable to structure 81 is in its deflated state, it may form a flattened shape and when inflated, the expandable structure 81 may inflate into a configuration which remains unsupported by or attached to the structure 83. Because the structure 83 may be formed of a member which solid along its length, the cryogen may be introduced directly into the expandable structure 81 through a distal opening defined in the probe shaft 145.

Alternatively, structure 83 may be formed of a hollow tubular member which itself is formed into the continuous or looped shape. In such an embodiment, the cryogen may be optionally introduced through the hollow tubular member and dispersed within the interior of the expandable structure 81 through one or more openings which may be defined along the tubular member. In yet another alternative, the structure 83 may be formed into a flattened shape rather than a looped shape. In this configuration, the structure may be either solid or hollow such that that cryogen may be introduced through the structure and into the interior of the expandable structure 81 via one or more openings defined along the structure.

The structure 83 may extend and remain attached to the probe shaft 145, but the remainder of the structure 83 which extends within the expandable structure 81 may remain unattached or unconnected to any portion of the expandable structure 81. Hence, once the expandable structure 81 is inflated by the cryogen, the structure 83 may be adjusted in position or moved via manipulating the probe shaft 145 relative to the interior of the expandable structure 81 to enable the targeted positioning and cooling of the tissue region when in contact against the outer surface of the expandable structure 81. For instance, the structure 83 may press laterally upon a particular region of the underlying tissue to stretch or thin out the contacted tissue region to facilitate the cryogenic treatment. When the structure 83 is adjusted in position relative to the expandable structure 81, the expandable structure 81 may remain in a static position against a contacted tissue region allowing for limited repositioning of the structure 83 within.

Alternatively in other variations, the structure 83 may be attached along the interior of the expandable structure 81 partially at particular portions of the structure 83 or along the entirety of the structure 83. For instance, structure 83 may be attached, adhered, or otherwise coupled over its entirety to expandable structure 81 while in other variations, a distal portion of structure 83 may be attached, adhered, or otherwise coupled to a distal portion of the expandable structure 81 while in yet other variations, portions of the structure 83 may be attached, adhered, or otherwise coupled to the expandable structure 81 along its side portions. Any of these variations may be optionally utilized depending upon the desired interaction and treatment between the structure 83, expandable structure 81, and underlying tissue region to be treated.

In yet another alternative variation, the lumen 84 for introducing the cryogen into the interior of the expandable structure 81 may be extended past the distal end of the probe shaft such that the cryogen is released within the interior at a more distal location. As shown, the cryogen lumen 84 may be supported along the structure 83, e.g., via a bar or member 85 which extends across the structure 83. This particular variation may allow for the cryogen to be introduced into the distal portion of the interior of the expandable member 81. Either this variation or the variation where the cryogen is released from an opening of the probe shaft may be utilized as desired.

Figure 11B:
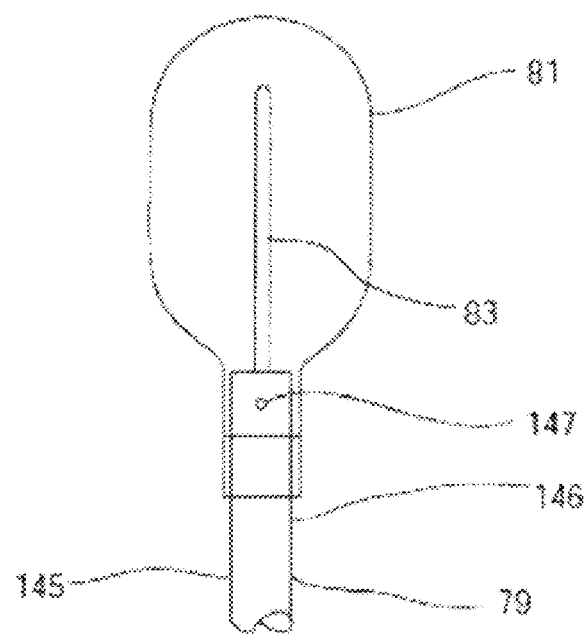
Figure 11C:
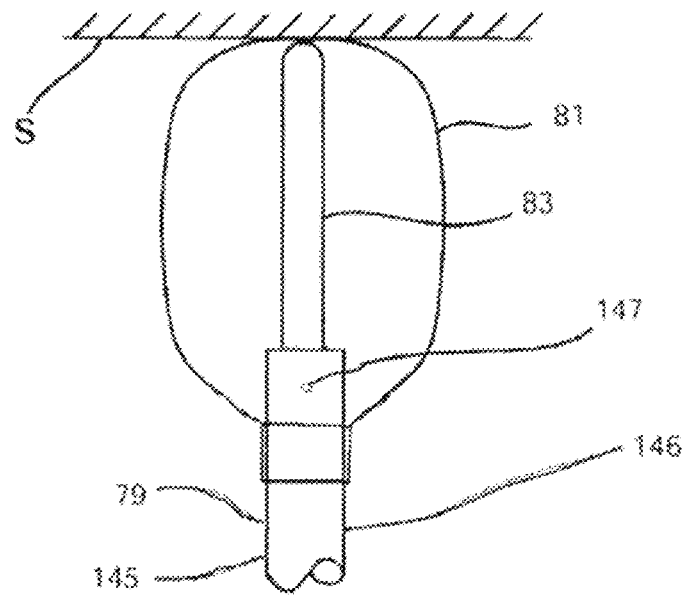
Figure 11D:
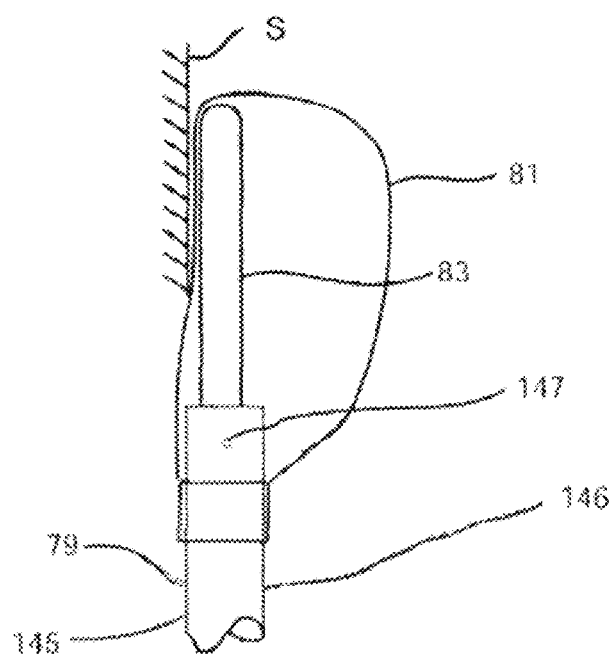

FIG. 11B shows a side view of the embodiment of FIG. 11A illustrating how the structure 83 can be formed from a relatively flattened configuration relative to the inflated expandable structure 81. Because of the structural integrity of structure 83 and its relatively flattened profile, the structure 83 may provide for targeted treatment of the tissue when contacted by the device. FIG. 11C shows the side view of the inflated expandable structure 81 when pressed in a longitudinal direction by its distal tip against the underlying tissue surface S. The relative strength of the structure 83 provides for the ability to press the device against the tissue surface such that the remainder of the expandable structure 81 may maintain its inflated configuration to potentially insulate the other surrounding tissue regions. FIG. 11D likewise shows the device when the structure 83 is pressed laterally along its side against the tissue surface S such that the structure 83 lies flat. The contacted tissue region may be treated while the remainder of the surrounding tissue is potentially insulated by the expanded structure 81.

While the treatment end effector is designed for application along the tissue region defined by the cul-de-sac, the same end effector may be used in other regions of the nasal cavity as well. For instance, once the ablation is performed along the cul-de-sac, the end effector may then be moved to an adjacent tissue region, e.g., region immediately inferior to the cul-de-sac, and ablation treatment may be effected again. Additionally and/or alternatively, the end effector may also be used to further treat additional tissue regions, e.g., posterior aspect of the superior, middle, and/or inferior turbinates (any one, two, or all three regions). In either case, once the cul-de-sac has been ablated, the end effector may remain in place until the tissue region has thawed partially or completely before the end effector is moved to the adjacent tissue region for further treatment.

Once the treatment is completed, or during treatment itself, the tissue region may be assessed utilizing any number of mechanisms. For instance, the tissue region may be visually assessed utilizing an imager during and/or after ablation.

As described herein, the device may be utilized with a temperature sensor, e.g., thermistor, thermocouple, etc., which may be mounted along the shaft, within or along the expandable structure 81, along the structure 83, etc., to monitor the temperature not only of the cryogen but also a temperature of the tissue region as well under treatment.

Additionally and/or alternatively, the expandable structure 81 may also be vibrated while maintaining the structure 83 against the interior of the expandable structure 81 and the tissue region utilizing any number of vibrational actuators which may be mounted anywhere along the device as appropriate. The vibrations may be applied directly against the tissue region or, e.g., through a layer of gel to facilitate the vibrational contact with the tissue.

Additionally and/or alternatively, other biocompatible agents may be used in combination with the cryogenic treatment. For instance, in one variation, an anesthetic may be applied to the tissue region to be treated prior to or during the cryogenic treatment. This and other alternative features described may be utilized not only with the variation shown and described in FIGS. 11A and 11B but with any other embodiments described herein and in previously incorporated U.S. Patent Application Publication No. 2015/0164571.

Figure 12A:
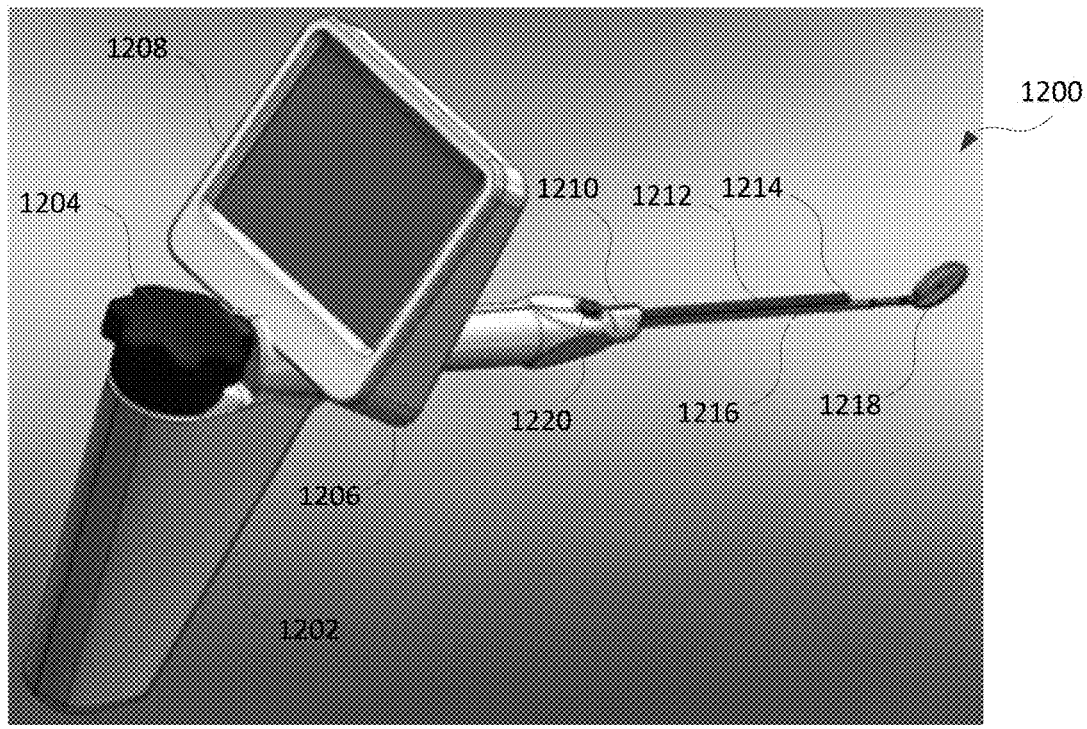
FIG. 12A is a perspective view of an integrated therapy and imaging device with a display, according to embodiments of the invention.
Figure 12B:
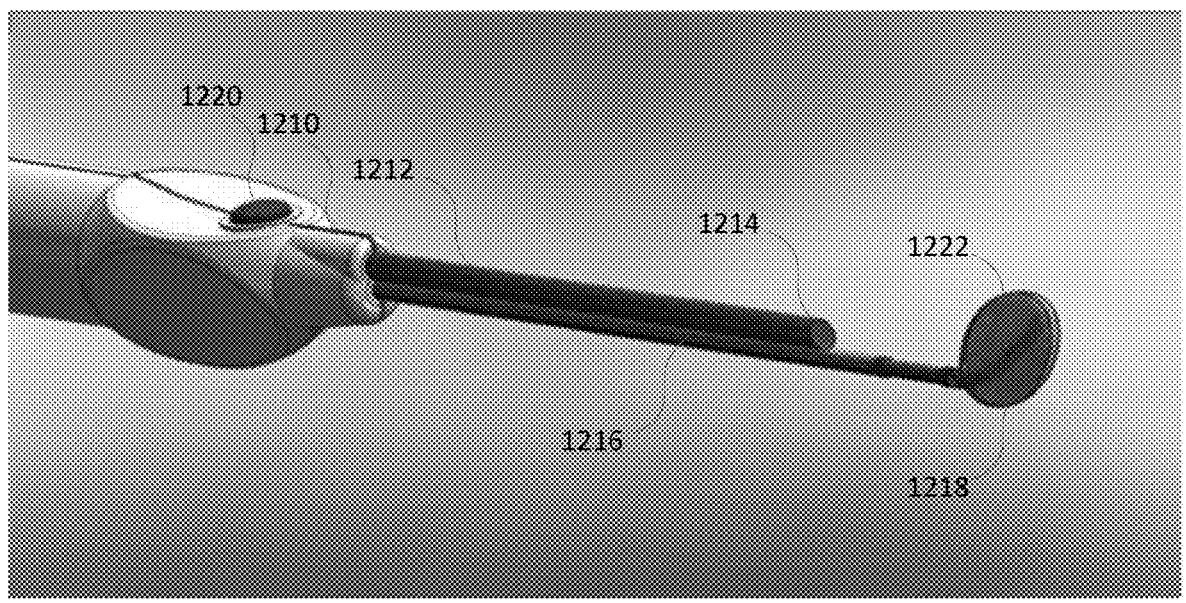
FIGS. 12B-E are perspective views of alternative embodiments of the distal end of the integrated therapy and imaging device of FIG. 12A, according to embodiments of the invention.

FIG. 12A is a perspective view of an integrated therapy and imaging device 1200 with a display 1208, and FIG. 12B is a perspective view of the distal end of the integrated therapy and imaging device of FIG. 12A, according to embodiments of the invention. Device 1200 may operate similarly to probe 1 described above, except that it may incorporate a display 1208 for ease of viewing during insertion of the distal end of device 1200 into a patient's nasal cavity.

With reference to FIG. 12A, it can be seen that handle 1202 includes an actuator 1220 that may cause cryogen contained in the cryogen container (not shown) housed in handle 1202 to flow through cannula 1216 to cryo-ablation element 1218. As can be seen in FIG. 12B, cryo-ablation element 1218 may be an inflatable structure with an internal structure 1222, which may be similar to expandable structure 81 and structure 83 described above with respect to FIGS. 11A-11D. Cannula 1216 extends from an opening in housing 1210 of device 1200.

Device 1200 also includes an imaging cannula 1212 that extends from the opening in housing 1210. Imaging cannula 1212 may have an imaging assembly 1214 disposed at the distal end thereof. Imaging assembly 1214 may include an imaging sensor (not shown) and light element (not shown) configured to provide visualization of cryo-ablation element 1218. For example, the imaging sensor of imaging assembly 1214 may be a CMOS imaging sensor, a CCD imaging sensor, or any other suitable sensor or sensors for detecting image information and converting that information into signals to be displayed on display 1208. Alternatively, imaging assembly may utilize one or more protected optic fibers that run within a lumen inside imaging cannula 1212 to a camera mount disposed on device 1200, at which point a CMOS or CCD imaging sensor may be coupled to the fibers. Light element of imaging assembly 1214 may include one or more LEDs disposed at the distal end of imaging cannula 1212, although other suitable light generating elements may also be used. Alternatively, one or more optic fibers that run within imaging cannula 1212 may be used to channel light to the working area around cryo-ablation element 1218. Such optic fibers may be coupled to one or more LEDs or other light generating elements integrated into handle 1202, or may be terminated at a standard ACMI adapter port to enable connection to an external light source as desired.

In order to be used in the nasal cavity, it may be preferable for the imaging assembly 1214 to have a field of view of at least 75 degrees and a viewing distance of at least 5 mm. Moreover, it may be preferable for imaging assembly 1214 to have an effective diameter of less than 2.5 mm.

Figure 12C:
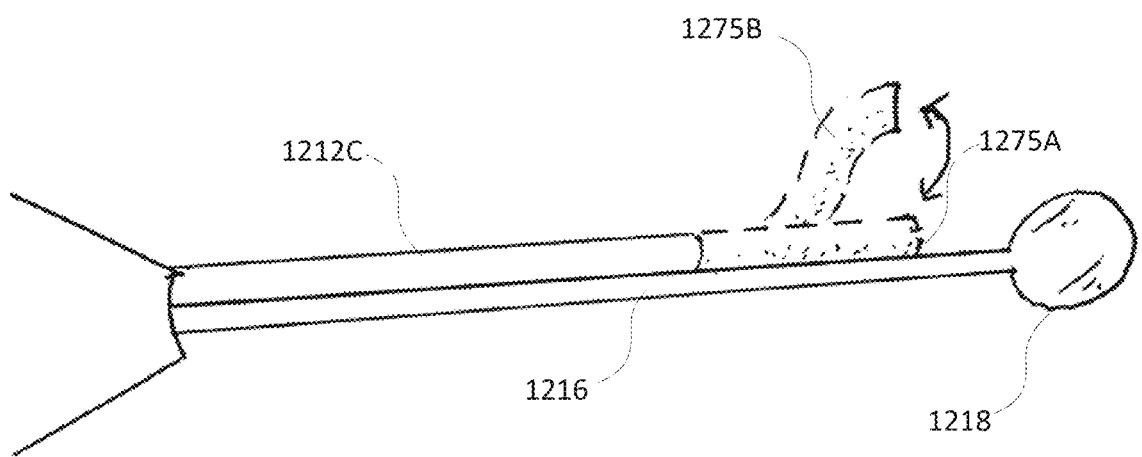
Figure 12D:
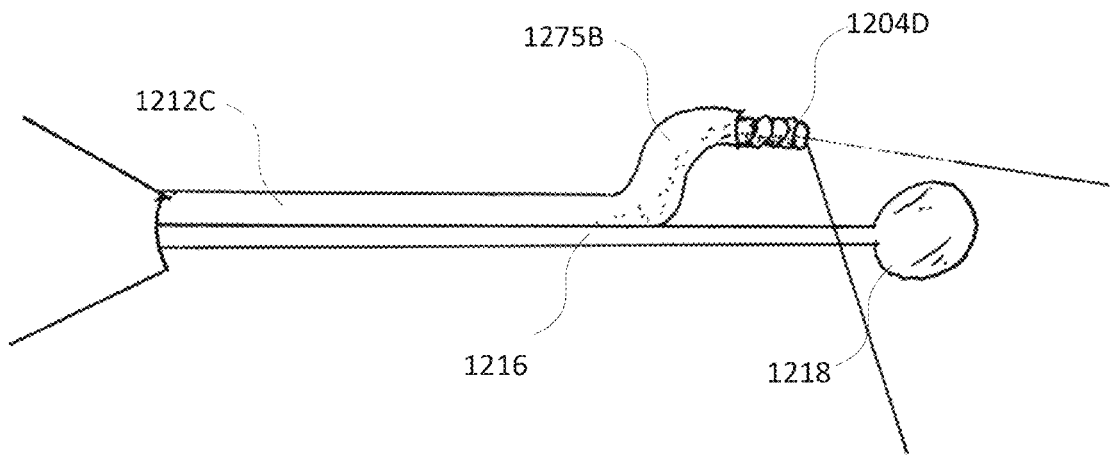

FIG. 12C shows an embodiment of the device 1200 with a malleable imaging cannula 1212C. Cannula 1212C may be constructed of malleable materials such as aluminum, copper, annealed steel, or some polymers. Cannula 1212C can be shaped in situ to a shape that is conducive to the desired field of view of the ablation element 1218. An initial shape is shown as 1275A, and an exemplary resulting shape is shown as 1275B. Once cannula 1212C takes the desired shape a flexible or elastic imaging component can be inserted into the cannula 1212C and then pushed forward until it exits the distal end of the cannula and naturally be in the proper location as defined by cannula 1212C apriori. FIG. 12D shows imaging assembly 1204D inserted through malleable imaging cannula 1212C after cannula 1212C has been formed into shape 1275B described above. Imaging assembly 1204D may be constructed of elastic material such as a spring coil or nitinol or an elastomer like silicone or polyurethane. The elastomeric property of this variation of assembly 1404D allows it to be easily inserted into the cannula 1212C described with reference to FIG. 12C and push out the distal end of malleable cannula 1212C.

Figure 12E:
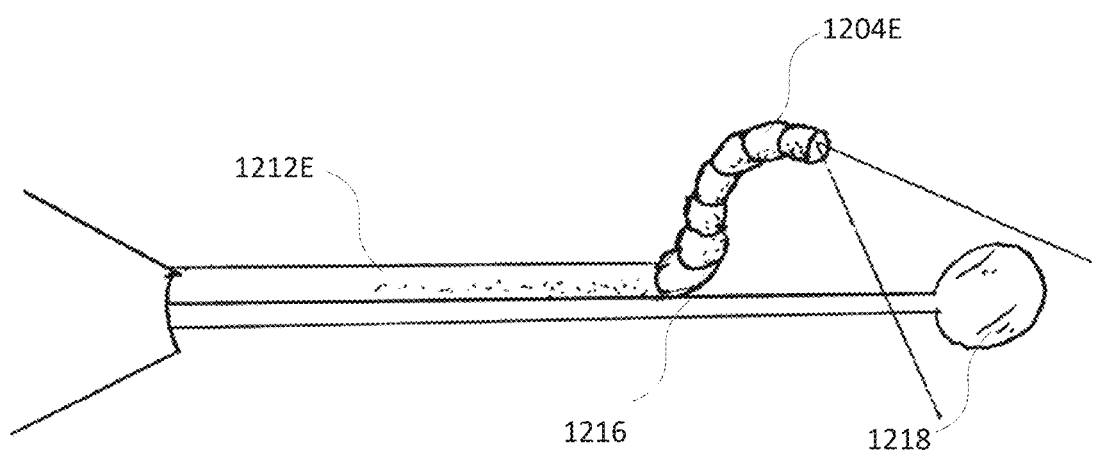

FIG. 12E shows another embodiment of device 1200 with a shape memory image assembly 1204E. Shape memory image assembly 1204E is made out of a material with shape memory such as spring steel, nitinol, shape memory polymers, or other suitable shape memory materials. Shape memory image assembly 1204E may have an original shape that allows a desired viewing angle and/or position relative to therapeutic element 1218. Shape memory image assembly 1204E may be inserted into cannula 1212E and be elastic enough to take a straight shape while moving through cannula 1212E, and take its original shape as it exits cannula 1212E. The original shape may be any suitable shape, and may have a curved, zigzag, or dogleg shape as needed.

Figure 13A:
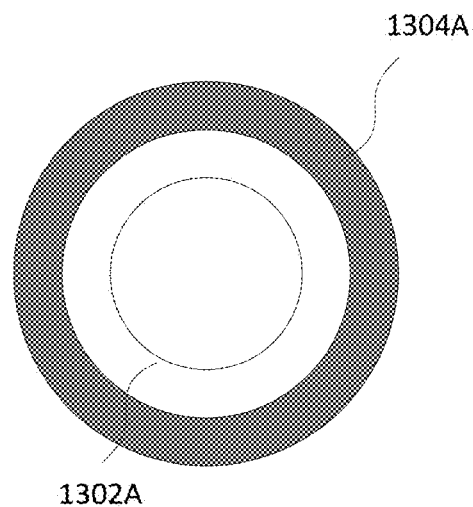
FIGS. 13A and 13B show simplified schematics of alternative arrangements of imaging sensors and light elements, according to embodiments of the invention.
Figure 13B:
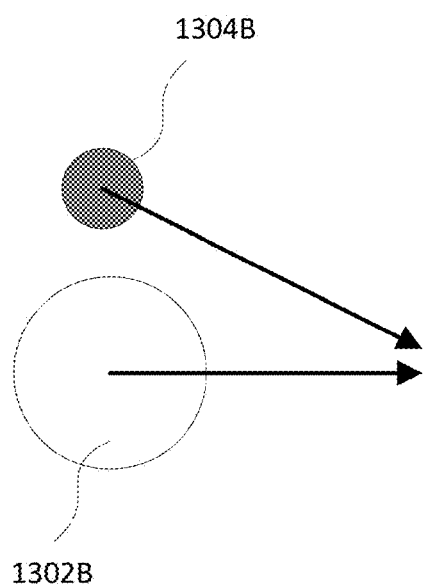

FIGS. 13A and 13B show simplified schematics of alternative arrangements of imaging sensors 1302 and light elements 1304, according to embodiments of the invention. It will be understood that these arrangements of imaging sensors 1302 and 1304 can be employed in imaging assembly 1214 or any other imaging assembly described herein. FIG. 13A shows a co-axial arrangement of imaging sensor 1302A and light element 1304A. For example, light element 1304A may be a ring of LEDs surrounding imaging sensor 1302A. FIG. 13B shows an off-axis arrangement, with light element 1304B directing light off-axis of imaging sensor 1302B.

Device 1200 may include an articulation actuator that is embedded or attached to device handle 1202, which may cause either or both of imaging assembly 1214 and/or cryoablation element 1218 to articulate in the manner described herein. For example, the actuator may be configured to cause an articulating region of cannula 1216 or imaging lumen 1212 to articulate as described with respect to FIGS. 1-9 and 14-21 herein.

As described above, device 1200 may include a display 1208 operably coupled to imaging assembly 1214. Display 1208 may be a smart phone, tablet, or other stand-alone display that can output video with a desired resolution. Display 1208 may be integrated with device 1200, or, alternatively, may be removably coupled from device 1200. For example, display 1208 may be removably coupled to display adapter 1206 by any suitable connection allowing attachment and detachment as needed by the user. For example, display adapter 1206 may include one or more magnetic elements that attract complementary magnetic elements on display 1208 to keep display 1208 in place as shown, but which allow a user to detach display 1208 as needed. Display adapter 1206 may also include the requisite electrical connections which connect display 1208 to imaging assembly 1204 and any components thereof. Thus, when connected to display adapter 1206, display 1208 can receive signals from imaging assembly 1204 and the components thereof to display cryo-ablation element 1218 and the surrounding areas during use of device 1200. The placement of display 1208 on device 1200 as shown may be preferable to using an external display at a remote location, since display 1208 may more easily fall in the line of sight of the healthcare provider during use of device 1200. This way, the healthcare provider will not need to look away from the patient when using device 1200.

Figure 14A:
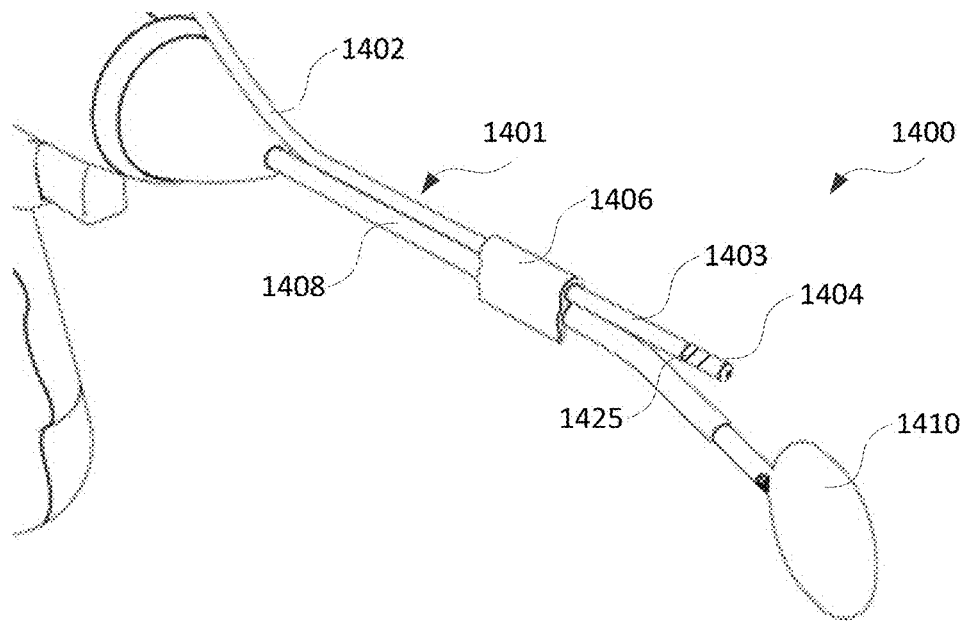
FIGS. 14A-14E show views of a distal end of an integrated therapy and imaging device, according to embodiments of the invention.

FIGS. 14A-14E show views of a distal end of an integrated therapy and imaging device 1400, according to embodiments of the invention. Device 1400 may be used to provide therapy in the nasal cavity as described above. For example, device 1400 may be used to deliver energy to tissue in the nasal cavity to ablate a posterior nasal nerve to treat rhinitis. As can be seen in FIG. 14A, device 1400 may have a therapeutic element 1410 for delivering the energy to tissue via working cannula 1408. For example, therapeutic element 1410 may be a cryo-ablation element as described previously.

In order to provide visualization of therapeutic element 1410 during positioning and treatment, an imaging attachment 1401 may be provided. Imaging attachment 1401 may include an imaging cannula 1402 with an imaging assembly 1404 disposed at the distal end of imaging cannula 1402. Imaging cannula 1402 and imaging assembly 1404 may generally be similar to imaging cannula 1212 and imaging assembly 1214 described above with respect to FIGS. 12A-12B, except that rather than extending from within a housing in device 1400, they are externally coupled to the working cannula 1408 via one or more couplers 1406. Couplers 1406 may be a C-shaped clip that keep imaging attachment 1401 coupled to working cannula 1408, but allow particular movement of imaging attachment 1401 and imaging assembly 1404 relative to therapeutic element 1410. For example couplers 1406 may be friction fittings that allow relative movement between working cannula 1408 and imaging cannula 1402, but only upon relative friction above a certain threshold. For example, the threshold relative friction may be ½ to 1 pound of force. This will allow the imaging cannula 1402 to remain coupled to working cannula 1408 during normal operation of device 1400, but still allow relative translation when desired upon minimal application of force by the user. Couplers 1406 may be made of polyurethane, latex, silicone, or other similar materials.

Although not shown in FIG. 14A, device 1400 may have a display disposed at the proximal end of the device that is operably coupled to the imaging assembly 1404 for visualization of the therapeutic element 1410. Alternatively, device 1400 may have a display adaptor disposed at the proximal end that is operably coupled to the imaging assembly 1404 via wiring or optical fibers disposed in imaging cannula 1402. The display adaptor may be configured to connect to any suitable external display for providing visualization of the images detected by imaging assembly 1404.

Figure 14B:
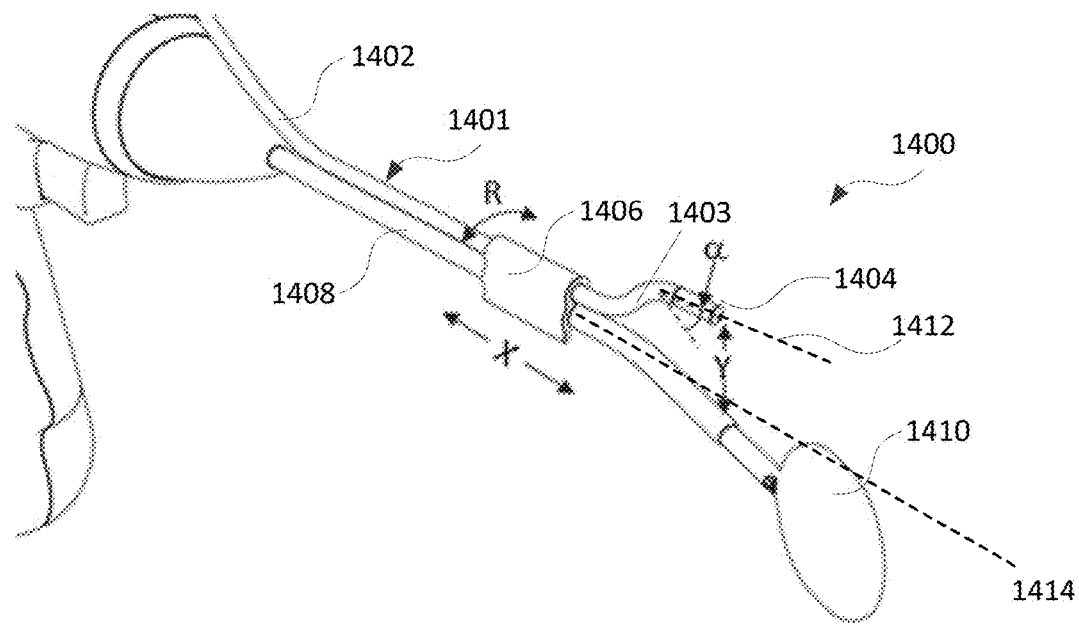

In order to view the therapeutic element 1410 from an optimal viewing angle or position, the imaging attachment 1401 may include an articulating region 1403 that is operably coupled to the imaging assembly 1404 and configured to articulate the imaging assembly 1404. As shown in FIG. 14B, imaging assembly 1404 may be configured to translate axially in the X direction to adjust the distance from therapeutic element 1410. Axial translation in this direction may range from about 5 mm to about 60 mm. Imaging assembly 1404 may also be configured to translate vertically in the Y direction to adjust the height of imaging assembly 1404 relative to working cannula 1408. Vertical translation in this direction may range from about 1 mm to about 10 mm. Imaging assembly 1404 may also be configured to laterally translate to adjust an angle α with respect to a central axis 1412 of imaging assembly. This may allow imaging assembly to obtain a desired viewing angle of therapeutic element 1410. This lateral translation may range from about 0 degrees to about 30 degrees. Additionally, imaging assembly 1404 may be configured to rotationally translate in the "R" direction about the insertion axis 1414 of the working cannula 1408. The range of rotation may be the entire 360 degrees about the insertion axis 1414, 0 to 180 degrees about the insertion axis 1414, or 45 degrees rotation about the insertion axis 1414 in either direction (from the initial position shown in FIG. 14A). This may allow imaging assembly 1404 to view therapeutic element 1410 from different vantage points as may be needed during use of device 1400. These degrees of freedom will also allow the imaging assembly 1404 to be positioned in a different location during insertion than during delivery of a therapeutic agent by therapeutic element 1410.

Because therapeutic elements such as cryo-ablation elements (or other ablation elements) may create extreme temperatures, imaging assembly may be coupled to a temperature control element 1425 (shown schematically in FIG. 14A). Temperature control element 1425 may include temperature sensors to detect the temperature of the imaging assembly 1404 and heating or cooling elements that can be controlled in response to the detected temperatures to maintain the imaging assembly within an operating temperature range during activation of therapeutic element 1410. For example, if device 1400 uses a cryoablation element, a heating element such as a heating coil may be provided to maintain imaging assembly within a suitable operating temperature. In some embodiments, the light element of imaging assembly 1404 may act as a heating element to keep imaging assembly within a suitable operating temperature. For example, one or more LEDs used as lighting elements may also be used has heating elements to keep imaging assembly 1404 (including image sensor) within a suitable operating temperature.

Figure 14C:
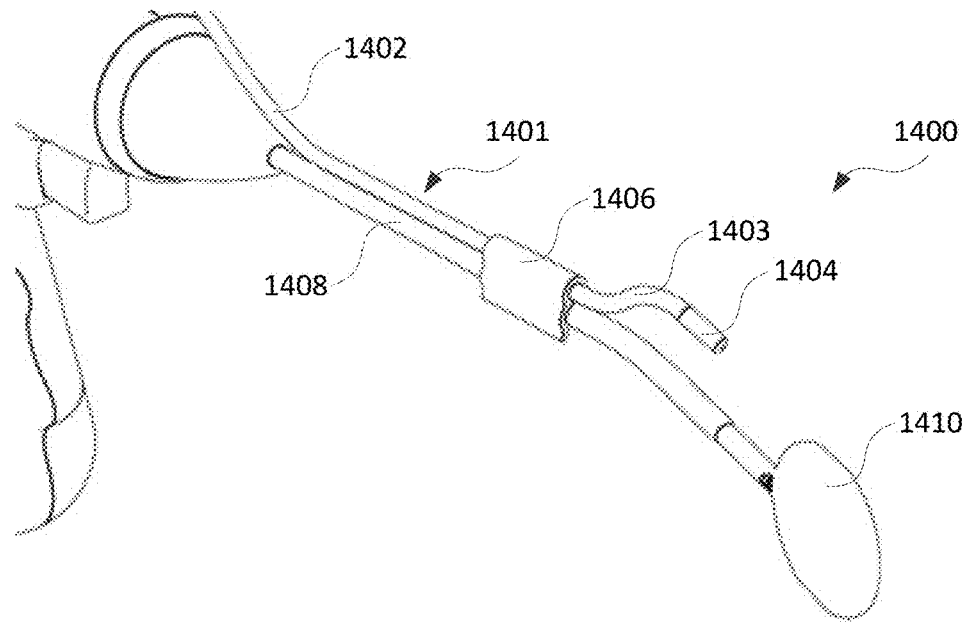
Figure 14D:
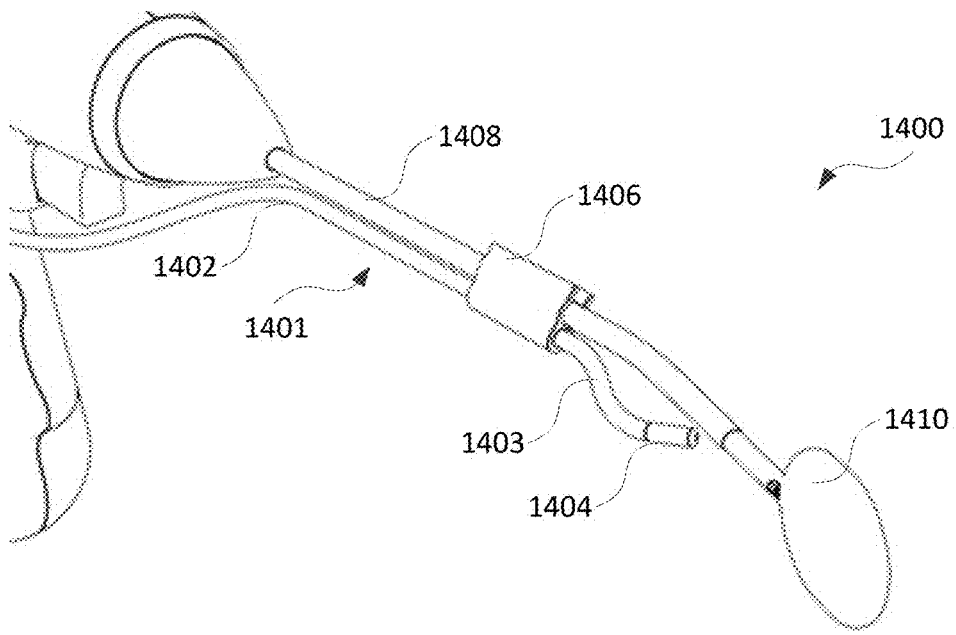

With reference back to FIG. 14A, it can be seen that imaging assembly 1404 may be in a default position prior to any articulation. In FIG. 14B, imaging assembly 1404 may be in an elevated position after vertical translation thereof. In FIG. 14C, imaging assembly 1404 may be both elevated vertically and angled laterally to point at therapeutic element 1410 from above. And, in FIG. 14D, imaging assembly 1404 is rotationally translated from the position in FIG. 14B. Although not shown in detail in FIGS. 14A-14D, in some embodiments, articulation of the imaging assembly 1404 may be effected using pullwires, slides, and/or dials that terminate at the proximal end of the device, where the user can manipulate the imaging assembly 1404 with their hand. For example, pullwires coupled to imaging assembly 1404 may extend through imaging cannula 1402 and may be tightened or loosened by the user using levers or other articulation actuators so as to cause articulating region 1403 to axially, vertically, laterally, and rotationally translate imaging assembly 1404 as desired. In some embodiments, axial and rotational translation may be directly caused manually by the user, while lateral and vertical translation may be actuated with levers coupled to guide wires.

As shown in FIGS. 14A-14D, imaging assembly 1404 may be disposed proximally of therapeutic element 1410 so as to minimize engagement with nasal tissue when the distal end of device 1400 is inserted into the nasal cavity. Specifically, imaging assembly 1404 may be dimensioned to fit within the profile dimensions of therapeutic element 1410 so that therapeutic element 1410 effectively protects imaging assembly from engagement with nasal tissue. Since therapeutic element 1410 has a predominantly vertical profile, it may be desirable to vertically stack imaging assembly 1404 and its components within this profile. Additionally, in some embodiments it may be desirable to limit the articulation of imaging assembly 1404 to remain within the profile of therapeutic element 1410.

Figure 14E:
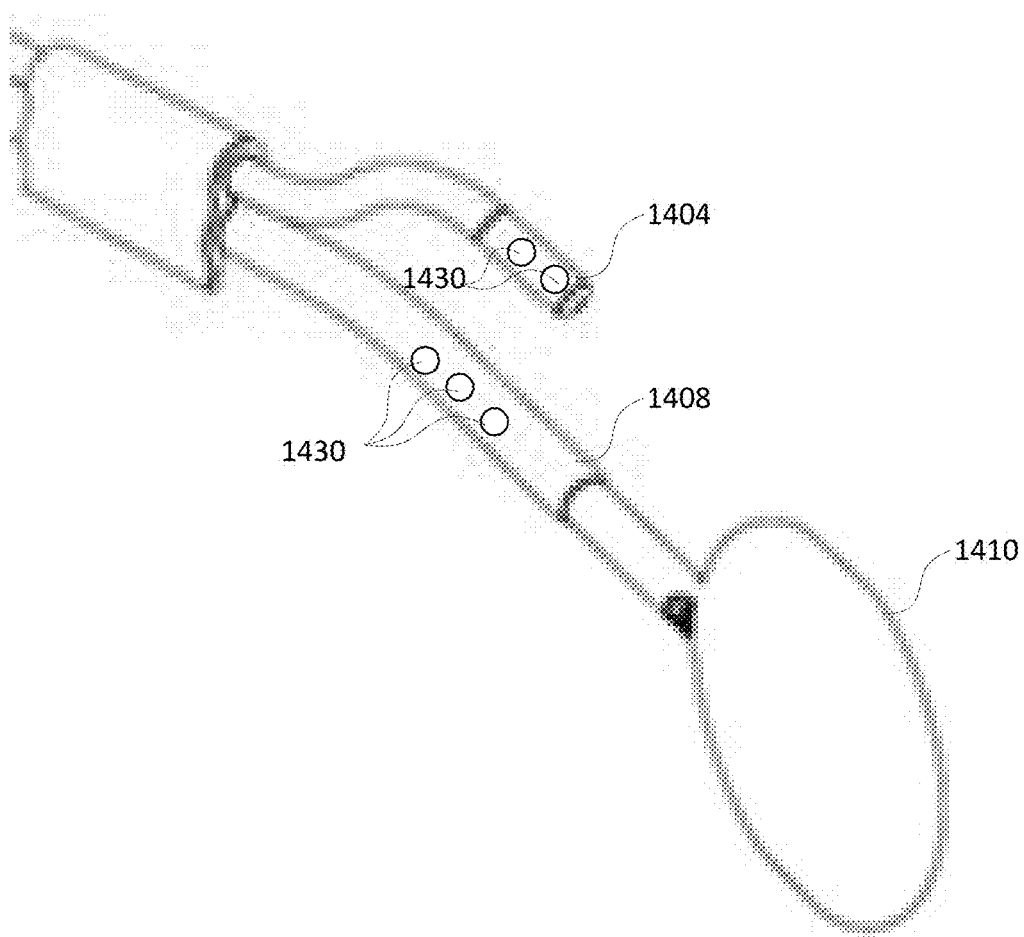

FIG. 14E shows a schematic illustration of one or more flushing and/or vacuum ports 1430 disposed on imaging assembly 1404 and/or working cannula 1408, according to embodiments of the invention. As can be seen in FIG. 14E, ports 1430 for flushing and/or vacuum may either embedded on working cannula 1408 or embedded on the body of the imaging assembly 1404. Ports 1430 may be fluidly coupled to channels within working cannula 1408 and/or imaging cannula 1402 to allow fluid to pass through, exit at the distal end of the working cannula 1408, and/or be sucked back outside the body. Although only shown schematically in FIG. 14E, flush ports 1430 may be designed to direct fluid at the imaging assembly 1404 and vacuum ports may be positioned about 180 degrees around the imaging assembly from the flush ports 1430 to catch fluid passing towards the imaging assembly 1404. The flush port inner lumen diameter may range from about 0.005 inches to 0.025 inches. The vacuum port inner lumen diameter may range from 0.005 inches to 0.025 inches and can be contoured to the outer edge of the imaging element.

Although not shown in FIGS. 14A-14E, it will be understood that multiple couplers 1406 may be used so that there are multiple attachment points between imaging attachment 1401 and working cannula 1408. In some embodiments, couplers 1406 may provide attachment points on articulating region 1403 so as to allow articulation of therapeutic element 1410 together with or independently of imaging assembly 1404.

A number of benefits of integrating an imaging attachment (such as imaging attachment 1401) with the aforementioned features can be appreciated. First, the integration of the imaging attachment with the therapeutic element may allow a user such as a healthcare provider to perform a therapeutic procedure with visualization using a single hand. This may decrease the time, cost, and labor involved in a given procedure, and may decrease the degree of difficulty for a given procedure. Second, the integration of the imaging attachment with the therapeutic procedure will improve the visualization of such a procedure, since it will ensure that the imaging will be able to reach sufficiently posterior to obtain detailed visualization of the target region. This is in contrast with rigid or flexible endoscopes which often do not allow imaging sufficiently close to the relevant working tool. Because the imaging attachment is coupled to the working device and can be manipulated to and then fixed at a desired position relative to the therapeutic element, it will assuredly reach posterior enough to provide sufficiently detailed imaging of the therapeutic element and target region.

Figure 15:
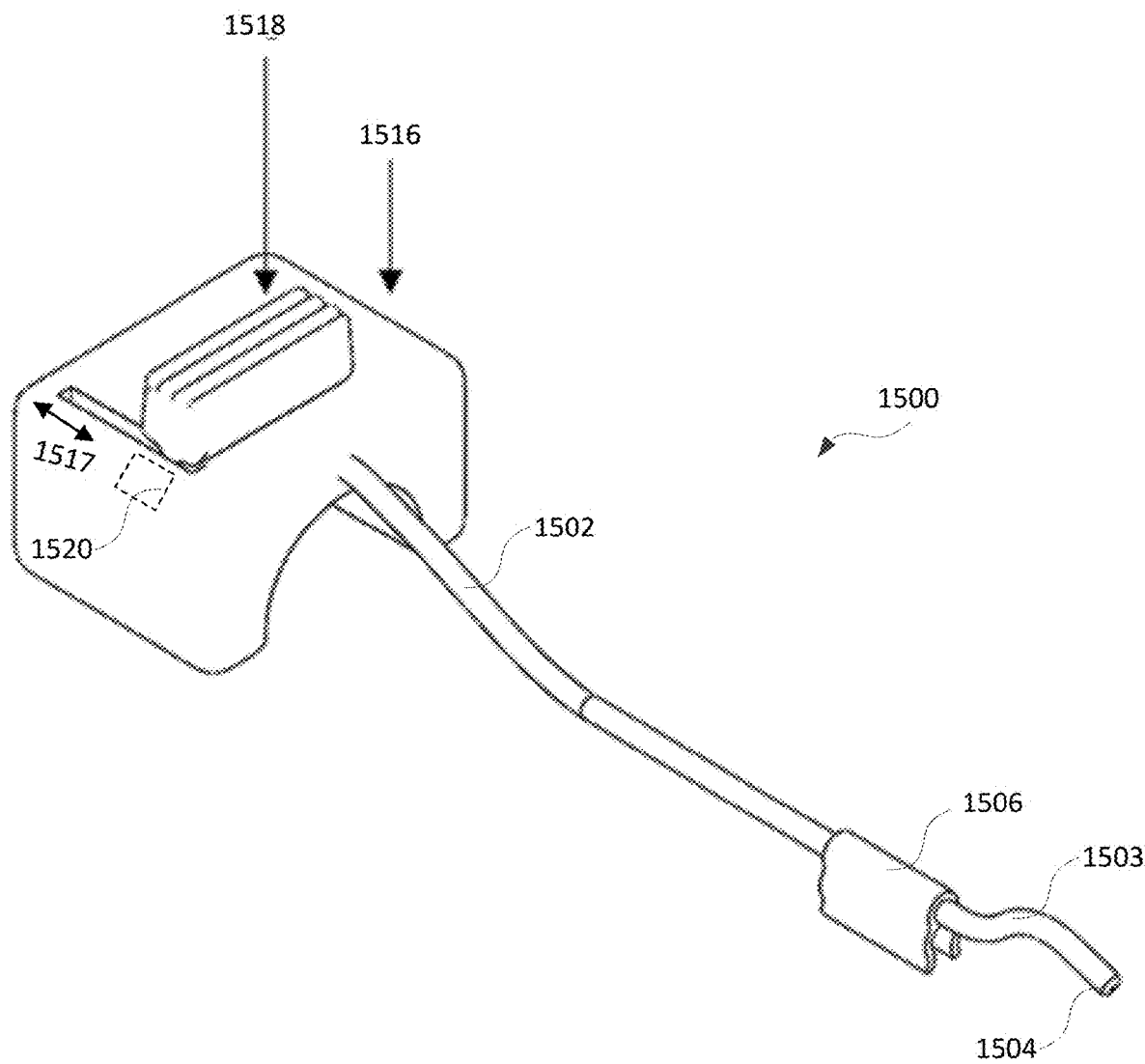
FIG. 15 shows a perspective view of an articulating imaging attachment, according to embodiments of the invention.

FIG. 15 shows a perspective view of an articulating imaging attachment 1500, according to embodiments of the invention. Articulating imaging attachment 1500 may include a handle attachment base 1516 which may connect imaging attachment 1500 to a handle of a therapeutic device as will be described with reference to FIGS. 16A-B, 17A-B, and 18A-B. Articulating imaging attachment 1500 may have an imaging cannula 1502 similar to imaging cannula 1402 described above, with an imaging assembly 1504, similar to imaging assembly 1404 described above, disposed at the distal end. Imaging cannula 1402 may be coupled to a working cannula of a device via one or more couplers 1506 similar to couplers 1406 described above. Articulating imaging attachment 1500 may also have articulating region 1503 similar to articulating region 1403.

In order to actuate the articulation of imaging assembly 1504, articulating imaging attachment 1500 may have a flexing lever 1518 that translates back and forth as shown by arrows 1517. Flexing lever 1518 may be coupled to pull wires housed in imaging cannula 1502 and coupled to imaging assembly 1504, so that when flexing lever is initially pulled in the proximal direction, the pull wire attached to the imaging assembly 1504 tightens and causes imaging assembly 1504 to vertically translate. As flexing lever 1518 reaches the last portion of travel (e.g. the last 2-3 mm), imaging assembly 1504 may stop vertically translating and may begin to laterally translate to angle image assembly 1504 relative to its central axis. The angle may range from about 0 to about 20 degrees from the central axis of imaging assembly 1504 without losing the vertical translation, similar to the lateral translation angle α described above with respect to imaging assembly 1404. Thus, it can be seen that flexing lever 1518 may allow for vertical and lateral translation of imaging assembly 1504. In order to lock imaging assembly 1504 at a desired viewing angle or position, a locking mechanism 1520 (shown schematically in FIG. 15) may be provided. Locking mechanism 1520 may be any suitable mechanism that keeps flexing lever 1518 in a desired position. For example, as the user translates flexing lever 1518 to a desired position, locking mechanism 1520 may automatically or upon actuation of a button or other mechanism keep flexing lever 1518 in the desired position so that the position and/or viewing angle of imaging assembly 1504 is fixed relative to the therapeutic element of the device that imaging attachment 1500 is attached to.

Imaging attachment 1500 may also allow axial and rotational translation of imaging assembly 1504 as described above with respect to imaging assembly 1404. In particular, handle attachment base 1516 may snap onto the handle of a therapeutic device 1600 as shown in FIGS. 16A-16B, 17A-17B, and 18A-18B. The connection between handle attachment base 1516 and device 1600 may allow base 1516 to translate axially in the X direction (shown in FIG. 16A) and rotationally in the R direction around the distal nose of the handle of device 1600 (shown in FIG. 16A) similar to the axial and rotational translation described with respect to imaging assembly 1404 above. In order to ensure one to one rotation between handle attachment base 1516 and imaging assembly 1504, the portion of imaging cannula 1502 extending from attachment base 1516 to coupler 1506 may be rigid. This way, the axial and rotational translation may be manually done by a user by axially translating and rotating attachment base 1516. The range of axial and rotational translation may be the same as described above with respect to imaging assembly 1404.

Figure 16A:
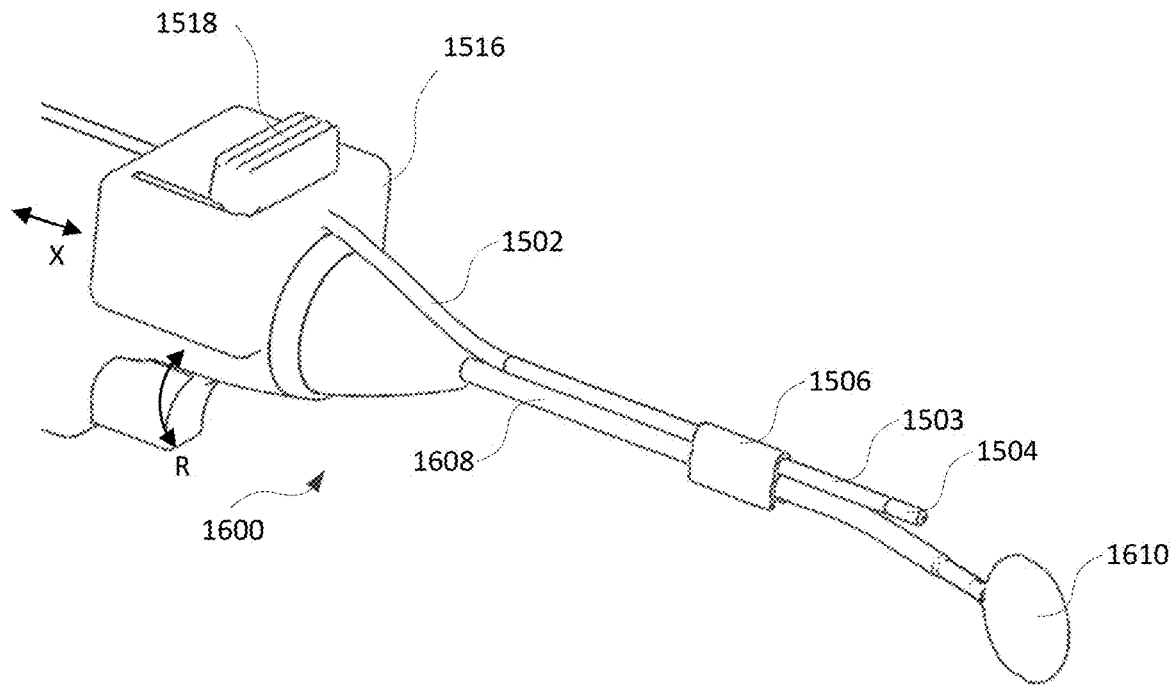
FIGS. 16A and 16B show views of a device with an integrated articulating imaging attachment in a non-articulated position, according to embodiments of the invention.
Figure 16B:
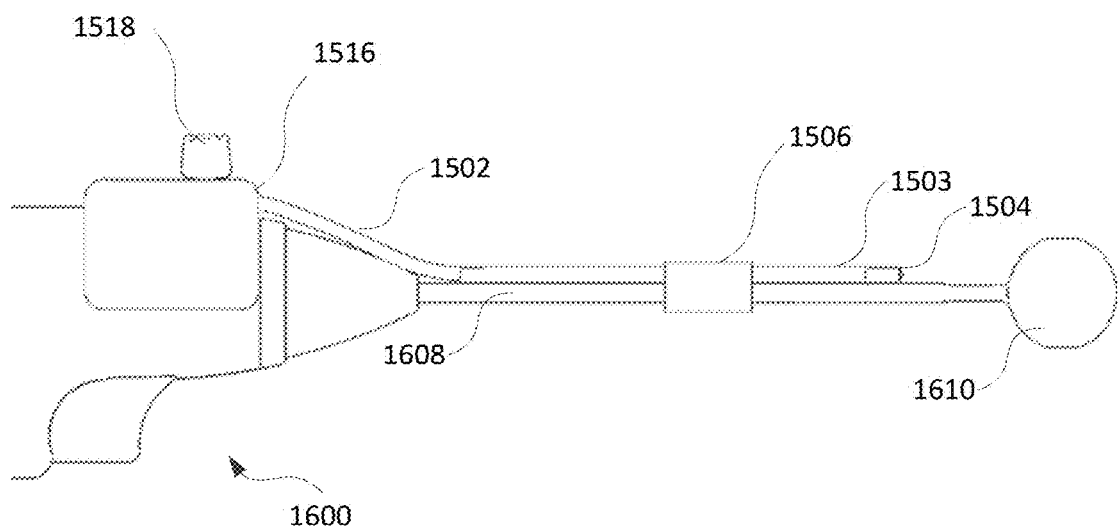

Vertical and lateral translation of imaging assembly 1504 will now be described with reference to FIGS. 16A-16B, 17A-17B, and 18A-18B. FIGS. 16A and 16B show views of a device 1600 with integrated articulating imaging attachment 1500 in a non-articulated position, according to embodiments of the invention. As can be seen in FIG. 16A, when imaging assembly 1504 is not articulated, flexing lever 1518 is in its most distal position. Upon pulling of flexing lever 1518 proximally (or in direction 1700 shown in FIG. 17A), imaging assembly 1504 may begin to articulate vertically.

Figure 17A:
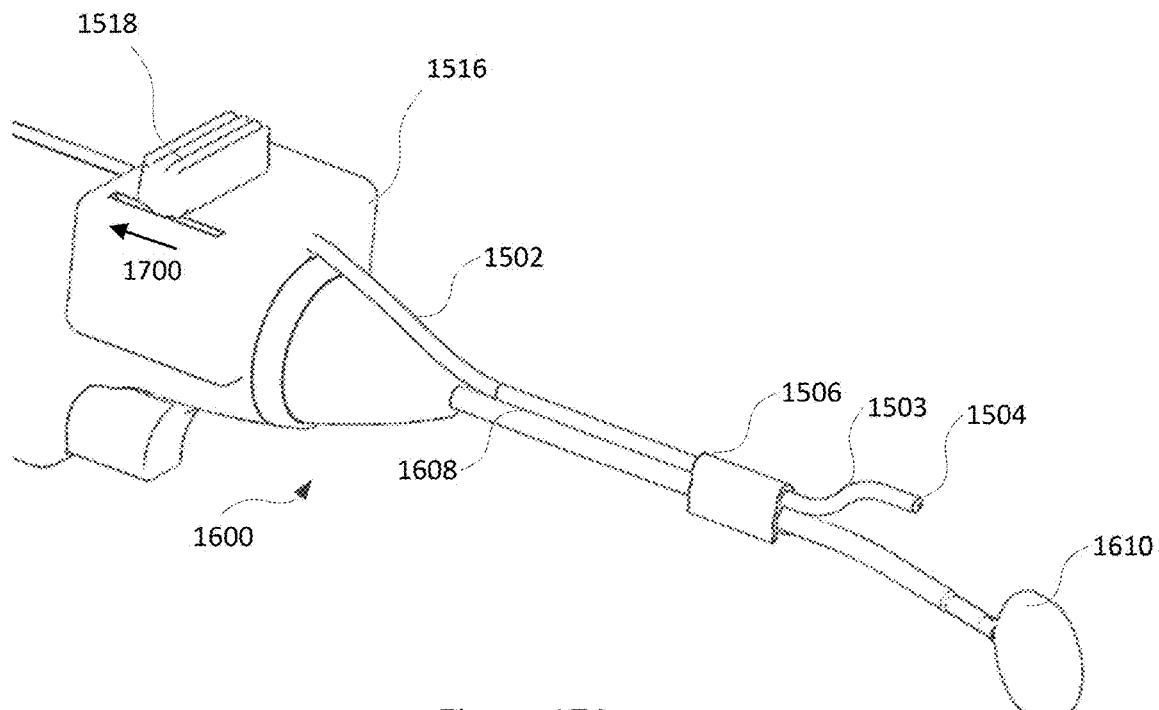
FIGS. 17A and 17B show views of device with an articulating imaging attachment in an elevated position, according to embodiments of the invention.
Figure 17B:
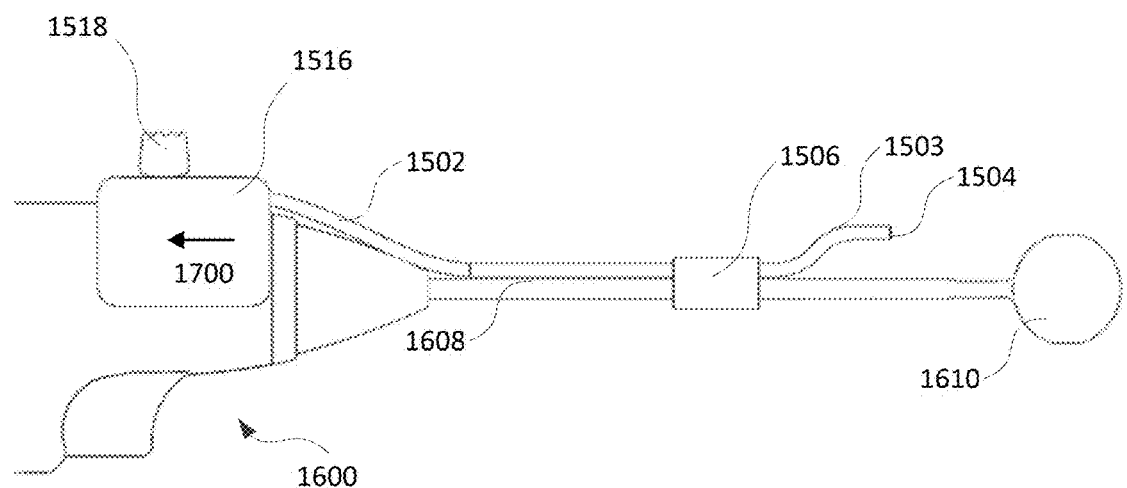

FIGS. 17A and 17B show views of device 1600 with articulating imaging attachment 1500 in an elevated position, according to embodiments of the invention. As can be seen in FIGS. 17A-17B, flexing lever 1518 is translated proximally in direction 1700 with respect to the position of flexing lever 1518 in FIGS. 16A-16B, and this translation has caused articulating region 1503 to bend, which has vertically translated imaging assembly 1504 at a height above working cannula 1608.

Figure 18A:
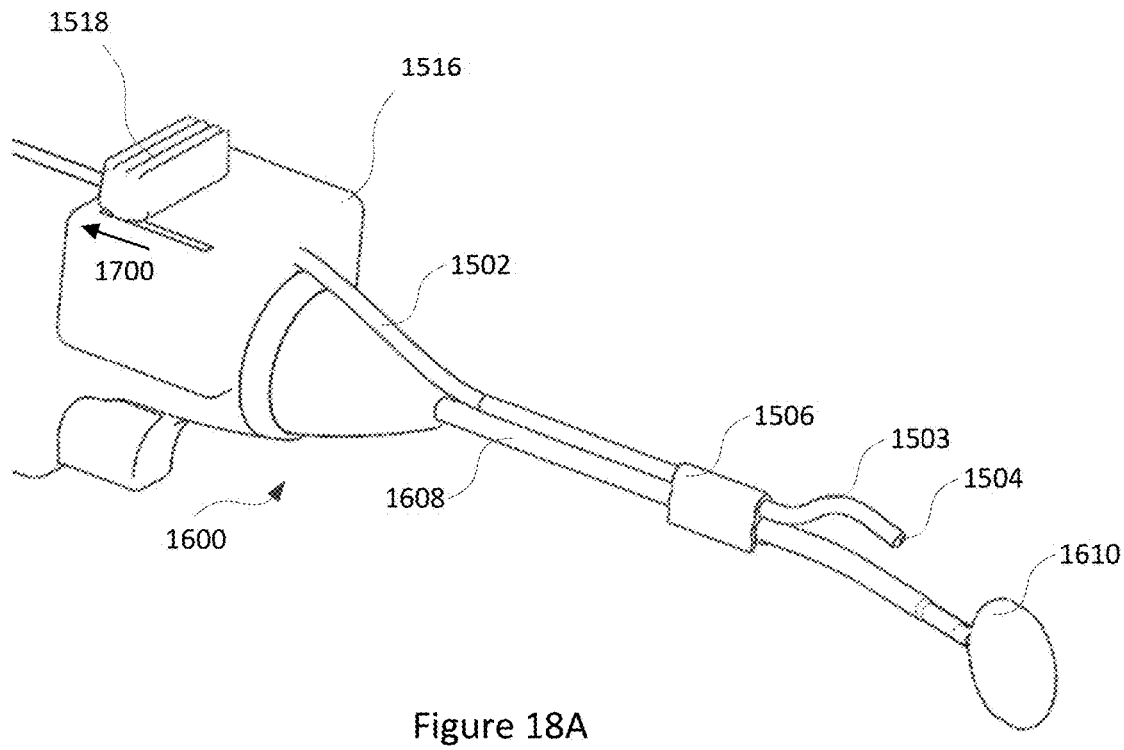
FIGS. 18A and 18B show views of device with an articulating imaging attachment in an elevated and downwardly angled position, according to embodiments of the invention.
Figure 18B:
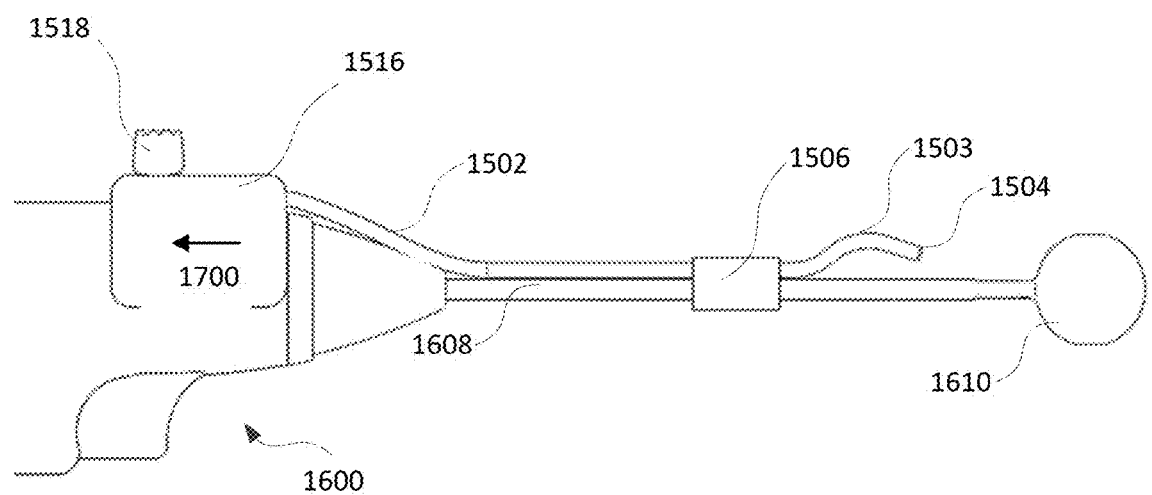

As described above, further translation of flexing lever 1518 in direction 1700 may cause lateral articulation of imaging assembly 1504 at an angle with respect to the central axis of imaging assembly 1504 without losing the vertical translation previously obtained. FIGS. 18A and 18B show views of device 1600 with articulating imaging attachment 1500 in an elevated and downwardly angled position, according to embodiments of the invention. As can be seen in FIGS. 17A-17B, flexing lever 1518 is translated at the most proximal location in direction 1700 with respect to the position of flexing lever 1518 in FIGS. 17A-17B, and this translation has caused articulating region 1503 to further bend, which has angled imaging assembly 1504 downwardly towards therapeutic element 1610.

FIG. 19 shows a perspective view of an imaging attachment 1900 with a malleable distal portion 1903, according to embodiments of the invention. Imaging attachment 1900 may be similar to imaging attachment 1500, except that rather than a lever-actuated articulating region, imaging attachment has a malleable distal portion 1903 on which imaging assembly 1904 is disposed, and a proximal rigid portion 1905 coupled to handle attachment base 1916. Rather than actuating articulation to adjust the position and/or viewing angle of imaging assembly 1904 as described in the embodiments above, the malleability of distal portion 1903 may allow this portion to be shaped (such as shape 1903A) by a user for a desired position and/or viewing angle of imaging assembly 1904. In some embodiments, proximal rigid portion 1905 may be made of a rigid steel, brass, aluminum, copper tubing, or rigid plastic, and malleable distal portion 1903 may be made of the same material as rigid portion 1905, but may be fully annealed, selectively annealed, thinned, or otherwise treated so as to be sufficiently malleable to be shaped by a user prior to use. Alternatively, the malleable distal portion 1903 may be made of a composite of polymer and metal. Malleable distal portion 1903 may be sufficiently malleable so as to be shaped by hand by a user, with or without application of additional energy such as heat. Once shaped as desired, malleable distal portion 1903 may remain semi-flexible, but generally maintain its shape in operation.

Because it may be desirable to have a particular shape of the malleable distal portion 1903 for a given procedure, a template may be used to shape the malleable distal portion 1903. The template may allow consistency across a number of healthcare providers or other users, while still allowing the users to provide a choice in the exact shape of the malleable distal portion 1903 so as to adjust the viewing angle and position of imaging assembly 1904 relative to a therapeutic element. FIGS. 20A and 20B show an exemplary template 2000 used to shape the malleable distal portion 1903 of imaging attachment 1900, according to embodiments of the invention. Template 2000 may have one or more shaping channels 2003 in which the malleable distal portion 1903 may be placed for shaping. Shaping channels 2003 may be designed to obtain a desired default shape for malleable portion 1903, which shape may provide an optimal position and/or angle with respect to a therapeutic element of a device. The user may then press the distal portion to follow the contours of shaping channel 2003 to obtain the desired shape for a given procedure. It will be understood that different templates may be generated and used for different procedures and/or different patients. For example, a given procedure may require a different shape to obtain an optimal position or angle, and thus a different template or a different shaping channel within the same template (as shown in FIG. 20) may be used to shape the malleable portion 1903. A single template such as template 2000 may have multiple shaping channels to account for variations in the anatomy while still providing a uniform shape across healthcare providers.

Figure 21A:
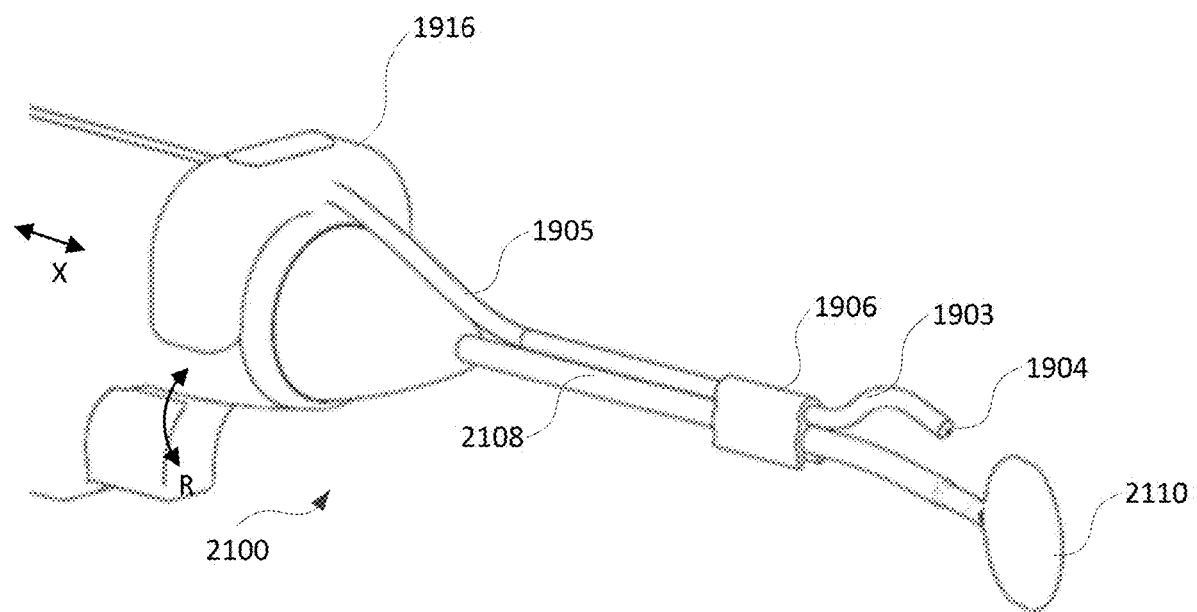
FIG. 21A shows a perspective view of a device with an integrated imaging attachment, according to embodiments of the invention.
Figure 21B:
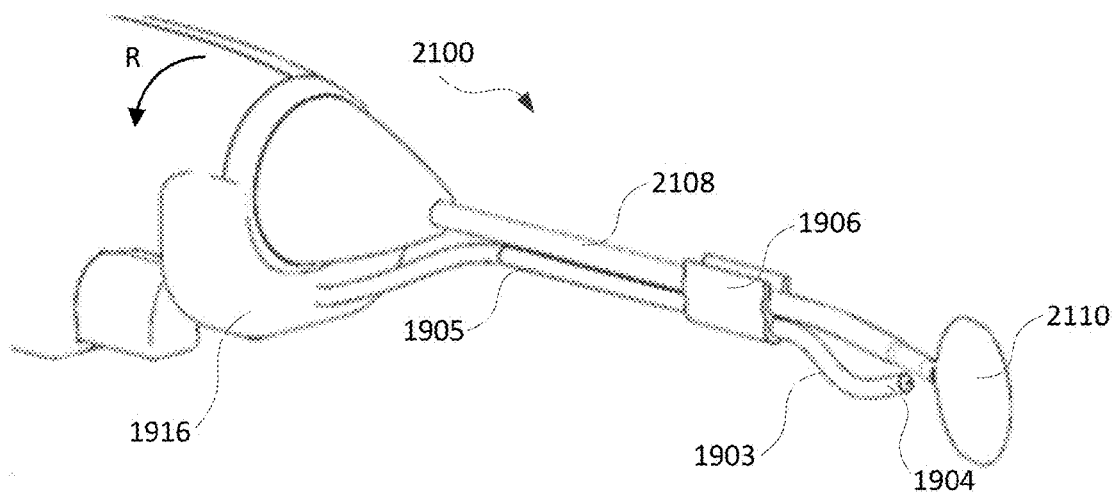
FIGS. 21B and 21C show perspective views of a device with an imaging attachment at various rotated positions relative to FIG. 21A, according to embodiments of the invention.
Figure 21C:
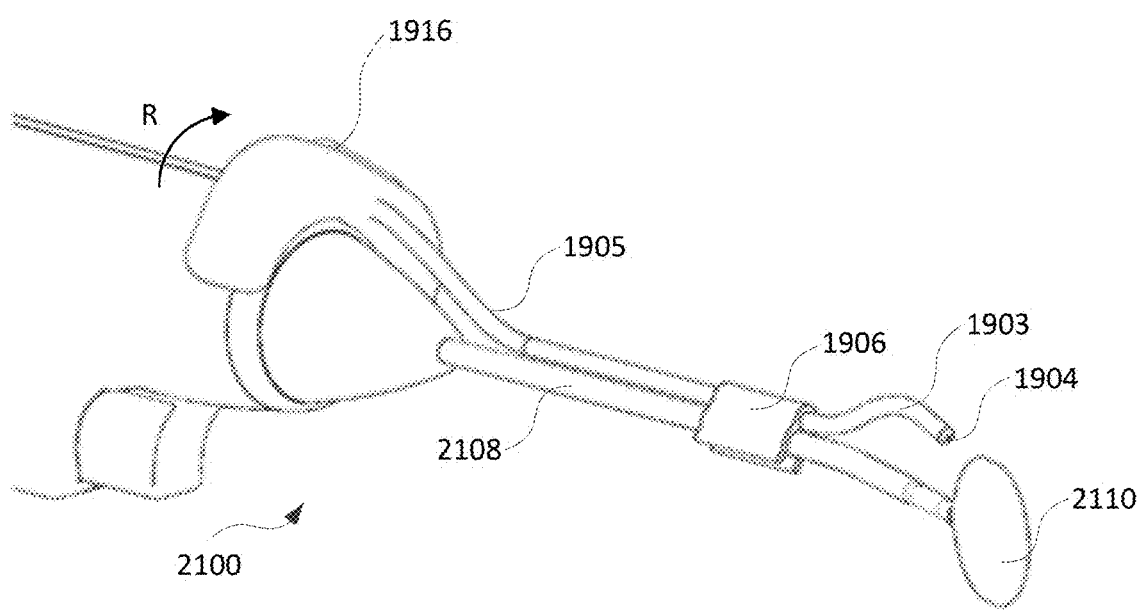

FIG. 21A shows a perspective view of a device 2100 with imaging attachment 1900, according to embodiments of the invention. Device 2100 may be a therapeutic device with a working cannula 2108 and therapeutic element 2110 disposed at the distal end, similar to the devices described above. As with imaging attachment 1500, handle attachment base 1916 of imaging attachment 1900 may snap onto the handle of device 2100, and the connection between handle attachment base 1916 and device 2100 may allow base 1916 to translate axially in the X direction (shown in FIG. 21A) and rotationally in the R direction around the distal nose of the handle of device 2100 (shown in FIG. 21A). The rigidity of portion 1905 will ensure one to one rotation between handle attachment base 1916 and imaging assembly 1904. This way, the axial and rotational translation may be manually done by a user by axially translating and rotating attachment base 1916. The range of axial and rotational translation may be the same as described above with respect to imaging assembly 1404 and imaging assembly 1504. Imaging attachment may also be coupled to cannula 2108 using a coupler 1906 similar to couplers described above. FIGS. 21B and 21C show perspective views of device 2100 with imaging attachment 1900 at various rotated positions relative to FIG. 21A, according to embodiments of the invention. As can be seen in FIGS. 21A-21C, imaging assembly 1904 remains in the same position and viewing angle as originally shaped, and merely rotates in the R direction to various positions about the axis of insertion of cannula 2108.

The applications of the disclosed invention discussed above are not limited to certain treatments or regions of the body, but may include any number of other treatments and areas of the body. Modifications of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A single handheld integrated therapy and imaging device, the device comprising:
    a handle including a handle housing with an opening;
    a working cannula extending from the opening of the handle housing, wherein an axis of the working cannula extends between a proximal portion of the working cannula at the opening of the handle housing and a distal portion of the working cannula, wherein the working cannula is a hollow elongated cannula;
    a therapeutic element coupled to the distal portion of the working cannula, wherein the therapeutic element includes a looped support structure defining a flattened shape with profile dimensions including (i) an axial dimension along the axis of the hollow elongated cannula, (ii) a vertical dimension perpendicular to the axial dimension, and (iii) a lateral dimension perpendicular to the axial dimension and the vertical dimension, the vertical dimension being greater than the lateral dimension;
    an imaging cannula external to the handle housing and coupled to the working cannula externally of the handle housing via one or more couplers;
    an imaging assembly disposed on the imaging cannula and configured to provide visualization of the therapeutic element; and
    an articulating region operably coupled to the imaging assembly and configured to articulate the imaging assembly relative to an axis of insertion of the working cannula into a nasal cavity,
    wherein the imaging assembly is arranged proximally from the therapeutic element and the imaging assembly is dimensioned to fit within the profile dimensions of the looped support structure such that the looped support structure protects the imaging assembly from nasal tissue during insertion of the device into a nasal cavity,
    wherein the imaging cannula includes a proximal portion removably coupled to the handle of the device by a handle attachment base, the handle attachment base configured for axial translation along a distal end of the handle and rotational translation about a central axis of the distal end of the handle.

2. The device of claim 1, wherein the articulating region is configured to vertically translate the imaging assembly so as to adjust a height of the imaging assembly relative to the axis of the working cannula.

3. The device of claim 2, wherein the articulating region is configured to adjust the height of the imaging assembly relative to the axis in a range from about 1 mm to about 10 mm.

4. The device of claim 1, wherein the articulating region is configured to axially translate the imaging assembly so as to adjust an axial position of the imaging assembly along the axis of the working cannula.

5. The device of claim 4, wherein the articulating region is configured to adjust the axial position in a range from about 5 mm to about 60 mm.

6. The device of claim 1, wherein the articulating region is configured to laterally translate the imaging assembly so as to adjust an angular position of the imaging assembly relative to a central axis of the imaging assembly.

7. The device of claim 6, wherein the articulating region is configured to adjust the angular position of the imaging assembly relative to the central axis of the imaging assembly in a range from about 0 degrees to about 30 degrees.

8. The device of claim 6, wherein the articulating region is configured to adjust the angular position of the imaging assembly relative to the central axis of the imaging assembly in a range from about 0 degrees to about 20 degrees while maintaining a height of the imaging assembly relative to the working cannula.

9. The device of claim 1, wherein the articulating region is configured to rotationally translate the imaging assembly about the axis of the working cannula.

10. The device of claim 1, wherein the articulating region is configured to vertically, axially, laterally, and/or rotationally translate the imaging assembly by user operation.

11. The device of claim 1, wherein the imaging assembly includes a detector and a light element.

12. The device of claim 1, wherein the imaging assembly comprises a detector and a light element that are co-axially arranged.

13. The device of claim 1, wherein the imaging assembly comprises a detector and a light element that are off-axis with respect to each other.

14. The device of claim 1, further comprising a locking mechanism configured to maintain a fixed position of the imaging assembly relative to the therapeutic element upon articulation of the imaging assembly to a desired viewing angle or position with respect to the therapeutic element.

15. The device of claim 1, wherein the imaging assembly is vertically stacked relative to the working cannula so as to protect the imaging assembly from engagement with the nasal tissue during insertion.

16. The device of claim 1, further comprising an image display disposed at a proximal end of the device and operably coupled to the imaging assembly for visualization of the therapeutic element on the image display.

17. The device of claim 1, further comprising a display adaptor disposed at a proximal end of the device and operably coupled to the imaging assembly.

18. The device of claim 17, further comprising a display coupled to the display adaptor for visualization of the therapeutic element on the display.

19. The device of claim 1 wherein the therapeutic element provides at least one of a cryo-ablation element, a radiofrequency ablation element, an ultrasonic ablation element, a laser ablation element, a microwave ablation element, and/or a chemo-ablation element.

20. The device of claim 19, further comprising a temperature control element coupled to the imaging assembly, the temperature control element configured to maintain the imaging assembly within an operating temperature range during activation of the therapeutic element.

21. The device of claim 1, wherein the therapeutic element comprises an expandable structure which is expandable from a deflated configuration to an expanded configuration, the looped support structure supporting the expandable structure.

22. The device of claim 1, further comprising at least one port configured to perform at least one operation selected from a group of operations consisting of: (i) direct a fluid or other agent into the nasal cavity and (ii) suction a fluid or other agent from the nasal cavity.

23. The device of claim 22, wherein the at least one port is disposed on the distal portion of the working cannula and fluidly coupled to a lumen of the working cannula.

24. The device of claim 22, wherein the at least one port is disposed on the imaging assembly.

25. A single handheld integrated cryo-therapy and imaging device for treatment of rhinitis, the device comprising:
a handle including a handle housing with an opening;
a working cannula extending from the opening of the handle housing, wherein an axis of the working cannula extends between a proximal portion and a distal portion of the working cannula;
a cryo-ablation element coupled to the distal portion of the working cannula, wherein the cryo-ablation element is expandable from a deflated configuration to an expanded configuration, the cryo-ablation element including a support structure with profile dimensions including (i) an axial dimension along the axis of the working cannula, (ii) a vertical dimension perpendicular to the axial dimension, and (iii) a lateral dimension perpendicular to the axial dimension and the vertical dimension, the vertical dimension being greater than the lateral dimension,
wherein, in the deflated configuration, the cryo-ablation element has a flattened shape defined by the profile dimensions of the support structure;
an imaging cannula external to the handle housing and coupled to the working cannula externally of the handle housing via one or more couplers;
an imaging assembly disposed on the imaging cannula and configured to provide visualization of the cryo-ablation element; and
an articulating region operably coupled to the imaging assembly and configured to articulate the imaging assembly relative to an axis of insertion of the working cannula into a nasal cavity,
wherein the imaging assembly is arranged proximally from the cryo-ablation element and the imaging assembly is dimensioned to fit within the profile dimensions of the support structure such that the support structure protects the imaging assembly from nasal tissue during insertion of the device into a nasal cavity, and
wherein the imaging cannula includes a proximal portion removably coupled to the handle of the device by a handle attachment base, wherein the handle attachment base is configured for at least one of:
axially translating the handle attachment base along a distal end of the handle so as to axially translate the imaging assembly, and/or
rotationally translating the handle attachment base about a central axis of the distal end of the handle so as to rotationally translate the imaging assembly about the axis of working cannula.

26. A method for treating rhinitis in a tissue region within a nasal cavity, the method comprising:
inserting a distal end of an integrated therapy and imaging probe into a nasal cavity of a patient, the probe comprising:
a handle including a handle housing with an opening,
a working cannula extending from the opening of the handle housing, wherein an axis of the working cannula extends between a proximal portion of the working cannula at the opening of the handle housing and a distal portion of the working cannula, wherein the working cannula is a hollow elongated cannula,
a therapeutic element coupled to the distal portion of the working cannula, wherein the therapeutic element includes a looped support structure defining a flattened shape with profile dimensions including (i) an axial dimension along the axis of the hollow elongated cannula, (ii) a vertical dimension perpendicular to the axial dimension, and (iii) a lateral dimension perpendicular to the axial dimension and the vertical dimension, the vertical dimension being greater than the lateral dimension,
an imaging cannula external to the handle housing and coupled to the working cannula externally of the handle housing via one or more couplers, an imaging assembly disposed on the imaging cannula and configured to provide visualization of the therapeutic element, and an articulating region operably coupled to the imaging assembly and configured to articulate the imaging assembly relative to an axis of insertion of the working cannula into a nasal cavity, wherein the imaging assembly is arranged proximally from the therapeutic element and the imaging assembly is dimensioned to fit within the profile dimensions of the looped support structure such that the looped support structure protects the imaging assembly from nasal tissue during insertion of the probe into a nasal cavity, and wherein the imaging cannula includes a proximal portion removably coupled to the handle of the probe by a handle attachment base, the handle attachment base configured for axial translation along a distal end of the handle and rotational translation about a central axis of the distal end of the handle articulating the imaging assembly relative to an axis of insertion of the working cannula into the nasal cavity until a desired viewing angle or position of the therapeutic element is obtained; and applying ablation therapy to a tissue region of a lateral nasal wall with the therapeutic element so as to treat rhinitis.

27. The method of claim 26, wherein articulating the imaging assembly comprises at least one of:

vertically translating the imaging assembly so as to adjust a height of the imaging assembly relative to the axis of the working cannula;

axially translating the imaging assembly so as to adjust an axial position of the imaging assembly along the axis of the working cannula;

laterally translating the imaging assembly so as to adjust an angular position of the imaging assembly relative to a central axis of the imaging assembly; or rotating the imaging assembly about the axis of working cannula.

28. The method of claim 26, further comprising locking a position of the imaging assembly relative to the therapeutic element upon articulation of the imaging assembly to the desired viewing angle or position with respect to the therapeutic element.

29. The method of claim 26, further comprising identifying the tissue region of the lateral nasal wall with the imaging assembly.

30. The method of claim 29, wherein identifying the tissue region of the lateral nasal wall with the imaging assembly comprises visualizing the tissue region on a display operably coupled to the imaging assembly.

31. The method of claim 26, further comprising articulating the therapeutic element of the probe so as to position the therapeutic element adjacent to the tissue region of the lateral nasal wall.

32. The method of claim 26, wherein applying ablation therapy to the tissue region of the lateral nasal wall comprises ablating at least one posterior nasal nerve within the tissue region of the lateral nasal wall with the therapeutic element.

33. The method of claim 32, wherein applying ablation therapy comprises delivering cryogenic energy, radio frequency energy, ultrasonic energy, light energy, microwave energy, or chemical energy to ablate the at least one posterior nasal nerve.

34. The method of claim 32, wherein the imaging assembly is maintained within an operating temperature range during ablation of the at least one posterior nasal nerve.

35. The method of claim 26, wherein the therapeutic element includes an expandable structure supported by the looped support structure and the method further comprising expanding the therapeutic element from a deflated configuration to an expanded configuration in contact against the tissue region of the lateral nasal wall.

36. The method of claim 35, wherein expanding comprises introducing a cryogenic fluid into the expandable structure such that it is inflated from the deflated configuration into the expanded configuration against the tissue region, wherein introducing the cryogenic fluid comprises evaporating the cryogenic fluid within the expandable structure so as to cryo-ablate at least one posterior nasal nerve.

37. The method of claim 26, wherein the probe comprises at least one port disposed at the distal end of the probe, the method further comprising at least one of:

providing fluid or other agent into the nasal cavity using the at least one port, and/or suctioning a fluid or other agent from the nasal cavity using the at least one port.

38. The method of claim 37, wherein the port is disposed at the distal end of the working cannula and fluidly coupled to a lumen within the working cannula.

39. The method of claim 37, wherein the port is disposed on the imaging assembly.

40. The method of claim 26, wherein articulating the imaging assembly comprises translating the imaging assembly such that the imaging assembly is positioned distal of the therapeutic element.

41. The device of claim 1, wherein the therapeutic element further comprises an expandable structure and the looped support structure is disposed in the expandable structure, and wherein the looped support structure has a rigidity that is suitable to maintain the flattened shape during insertion of the device in the nasal cavity.

42. The device of claim 1, wherein the looped support structure is formed from a wire.

43. The device of claim 1, wherein the looped support structure is formed from a hollow tubular member.

44. The device of claim 1, wherein the one or more couplers are configured to allow articulation of the therapeutic element together with the imaging assembly when a force applied to the imaging cannula relative to the working cannula is below a threshold, and the one or more couplers are configured to allow the imaging assembly to move vertically, axially, laterally, and/or rotationally relative to the therapeutic element when the force applied to the imaging cannula relative to the working cannula is above the threshold.

45. The device of claim 1, wherein one of the one or more couplers is configured to: (i) couple the articulating region to the working cannula, (ii) move the therapeutic element on the working cannula together with the imaging assembly when a force applied to the imaging cannula relative to the working cannula is below a threshold, and (iii) allow the imaging assembly to move relative to the therapeutic element when the force applied to the imaging cannula relative to the working cannula is above the threshold.

* * * * *